(12) United States Patent
Horlick et al.

(10) Patent No.: US 6,469,150 B1
(45) Date of Patent: Oct. 22, 2002

(54) CLONING AND CHARACTERIZATION OF GENES ENCODING BRADYKININ $B_1$ RECEPTOR HOMOLOGUES FROM FIVE MAMMALIAN SPECIES

(75) Inventors: Robert Horlick, Cambridge, MA (US); Jiuqiao Zhao, Hockessin, DE (US); Robert Swanson, Cranbury, NJ (US); Maria Webb, Flemington, NJ (US); Barbara Strohl, Hamilton, NJ (US)

(73) Assignee: Pharmacopeia, Inc., Cranbury, NJ (US)

( * ) Notice: Subject to any disclaimer, the term of this patent is extended or adjusted under 35 U.S.C. 154(b) by 0 days.

(21) Appl. No.: 09/576,160

(22) Filed: May 22, 2000

(51) Int. Cl.[7] .............................. C07H 21/04; C12Q 1/68
(52) U.S. Cl. ..................... 536/23.1; 536/23.5; 435/6; 435/69.1; 435/252.3; 435/320.1
(58) Field of Search .................. 435/6, 69.1, 252.3, 435/320.1; 536/23.1, 23.5

(56) References Cited

U.S. PATENT DOCUMENTS

| | | | | |
|---|---|---|---|---|
| 5,712,111 A | * | 1/1998 | Linemeyer et al. | ......... 435/69.1 |
| 5,965,367 A | | 10/1999 | Linemeyer et al. | ............ 435/6 |

OTHER PUBLICATIONS

Judith M. Hall, "Bradykinin Receptors," Gen. Pharmac., 28 (1) 1–6 (1997).

Jones et al., "Molecular characterisation of cloned bradykinin B1 receptors from rat and human," European Journal of Pharmacology, 374 423–433 (1999).

Ni et al., "Molecular cloning and expression of rat bradykinin B1 receptor," Biochimica et Biophysica Acta 1442 177–185 (1998).

Pesquero et al., "Molecular Cloning and Functional Characterization of a Mouse Bradykinin B1 Receptor Gene," Biomedical and Biophysical Research Communications, 220 219–225 (1996).

Menke et al., "Expression Cloning of a Human B1 Bradykinin Receptor," J. Biol. Chem., 269, (34) 21583–21586 (1994).

GenBank Accession No. AJ132230, Jones et al., Eur. J. Pharmacol. 374 (3) 423–433 (1999).

GenBank Accession No. X69681, McIntyre, P., Mol. Pharmacol. 44 (2) 346–355 (1993).

MacNeil et al., "Cloning and pharmacological characterization of a rabbit bradykinin B1 receptor," Biochimica et Biophysica Acta 1264 223–228 (1995).

GenBank Accession No. U47281, Pesquero et al., Biochem. Biophys. Res. Commun. 220 (1) 219–225 (1996).

GenBank Accession No. U44436, Yanagawa et al., "Novel pharmacological selectivity of the cloned murine B1 bradykinin receptor," unpublished.

GenBank Accession No. L42383, Chai et al., Genomics 31 (1) 51–57 (1996).

GenBank Accession No. U12512, Menke et al., J. Biol. Chem. 269 21583–21586 (1994).

GenBank Accession No. NM_000710, Menke et al., J. Biol. Chem. 269 21583–21586 (1994).

* cited by examiner

*Primary Examiner*—Lisa B. Arthur
*Assistant Examiner*—Jeanine Goldberg
(74) *Attorney, Agent, or Firm*—Heslin Rothenberg Farley & Mesiti P.C.

(57) ABSTRACT

The genes for bradykinin $B_1$ receptor from five mammalian species, vervet monkey, rhesus macaque, tree shrew, dog and pig have been cloned and characterized. In addition to the delineation of the nucleotide and amino acid sequences, methods for identifying modulators of bradykinin $B_1$ receptor activity using these molecules is also described. Additionally, a method for identifying an animal model useful in the screening of potential therapeutic agents is provided.

8 Claims, 15 Drawing Sheets

Pair Distances of B1 Protein Sequences From Nine Species

| Human | Vervet | Rhesus | Tree Shrew | Dog | Rabbit | Pig | Mouse | Rat | |
|---|---|---|---|---|---|---|---|---|---|
| *** | 96 | 96.3 | 80.5 | 75.3 | 77.1 | 72.3 | 71 | 68.6 | Human |
| | *** | 97.7 | 80.5 | 75 | 77.3 | 73.1 | 71.3 | 68.6 | Vervet |
| | | *** | 81.6 | 75 | 77.3 | 73.1 | 70.7 | 68.3 | Rhesus |
| | | | *** | 71.9 | 75.9 | 70.3 | 70.4 | 68.6 | Tree Shrew |
| | | | | *** | 71.9 | 69.4 | 67.8 | 66.9 | Dog |
| | | | | | *** | 72.2 | 72.2 | 67.8 | Rabbit |
| | | | | | | *** | 67.2 | 64.5 | Pig |
| | | | | | | | *** | 88.1 | Mouse |
| | | | | | | | | *** | Rat |

Dog sequence is from amino acid 1-320 only. Numbers represent percent identity.

Average Kd values for dALKd

| orthologue | Avg Kd ± SEM | n= |
|---|---|---|
| hB1 | 0.6 ± 0.1 | 7 |
| mB1 | 2.8 ± 1.0 | 5 |
| LB1 | 1.3 ± 0.1 | 3 |
| tB1 | 4.2 ± 1.0 | 2 |
| pB1 | 1.9 ± 0.7 | 3 |
| dB1 | 3.3 ± 0.2 | 2 |

Average Ki values in nM

| | Human | Rabbit | ree Shre | Rhesus | Pig | Dog |
|---|---|---|---|---|---|---|
| dAKd | 1.5 ± 0.7 | 3.4 ± 1.0 | 6.1 ± 1.2 | 3.3 ± 2.4 | 2.3 ± 1.0 | 4.2 ± 1.2 |
| Bk | IA | IA | IA | IA | IA | IA |
| dALKd | 4.6 ± 2.1 | 9.3 ± 1.5 | 22 ± 6 | 9.5 ± 5.3 | 9.5 ± 2.7 | 120 ± 36 |
| dABk | IA | 248 ± 139 | IA | IA | 218 ± 94 | 7.6 ± 1.2 |
| PS309799 | 17.3 ± 1.5 | IA | 3.3 ± 0.9 | 22.8 ± 4.6 | IA | IA |
| PS596668 | 5.7 ± 1.5 | 27.7 ± 6.4 | 0.6 ± 0.2 | 13.0 ± 5.1 | 33.3 ± 8.9 | IA |
| PS972282 | 6.3 ± 0.4 | 15.1 ± 8.4 | 0.9 ± 0.1 | 7.5 ± 1.1 | 22.5 ± 8.1 | 50.3 ± 6.7 |
| PS978163 | 6.3 ± 1.1 | 20.8 ± 5.9 | 0.9 ± 0.2 | 10.3 ± 5.6 | 63.7 ± 24.6 | 363 ± 57 |

309799    tree shrew > human > Rhesus macaque >> pig > dog, rabbit
596668    tree shrew > human > Rhesus macaque > rabbit > pig >> dog
972282    tree shrew > human = Rhesus macaque > rabbit > pig > dog
978163    tree shrew > human > Rhesus macaque > rabbit > pig > dog

CLONING AND CHARACTERIZATION OF GENES ENCODING BRADYKININ B₁ RECEPTOR HOMOLOGUES FROM FIVE MAMMALIAN SPECIES

FIELD OF THE INVENTION

The invention relates to nucleotide sequences encoding bradykinin $B_1$ receptors, recombinant expression vectors containing the genetic information, recombinant host cells capable of expressing the receptors and methods for identifying modulators of bradykinin $B_1$ receptor activity.

BACKGROUND OF THE INVENTION

The bradykinin (BK) $B_1$ receptor, first identified in 1977, has been postulated to play a major role in the pathophysiology of chronic pain and inflammation. With some exceptions, most notably in several tissues in dog, the $B_1$ receptor is not generally present unless its expression is induced by trauma or inflammatory stimuli. Following its induction, evidence suggests that the $B_1$ receptor upregulates and maintains its own expression via an autocrine feedback loop upon occupation by its native ligands, des-$Arg^{10}$-kallidin (dAKd) or, in the case of rodents, des-$Arg^9$-BK (dABk). The autocrine nature of $B^1$ receptor expression, coupled with the fact that the receptor is not generally expressed in normal, non-traumatized tissues, makes this an attractive target for anti-inflammatory and antinociceptive therapy.

In classical approaches to drug discovery, the activity of compounds are typically first analyzed by direct in vivo administration into test animals, or alternatively, in vitro using animal tissues. These avenues of discovery often lead to the identification of compounds potent in the test animal but of unknown efficacy in humans. In more recent paradigms of drug discovery, screening efforts are typically conducted on cloned human targets but resulting properties of lead candidates are sometimes complicated by lack of efficacy in animal models of choice.

The problem of potent but highly species-specific compounds is being encountered with greater frequency as the use of cloned human receptors in high-throughput drug screening becomes standard procedure. What is needed is an approach to address this problem by (1) looking at in vitro predictors of in vivo efficacy in animals and (2) screening molecules potent at the human receptor for activity at various animal orthologues in order to identify dually active compounds and an animal model useful in early efficacy studies of potential drug candidates.

SUMMARY OF THE INVENTION

In one aspect, the invention relates to a purified DNA molecule encoding a bradykinin $B_1$ receptor from one of five mammalian species. The invention includes DNA molecules encoding an amino acid sequence chosen from SEQ ID NO: 1, SEQ ID NO: 2, SEQ ID NO: 3, SEQ ID NO: 4, and SEQ ID NO: 5 and functional derivatives thereof.

In another aspect, the invention relates to a purified DNA molecule having a nucleotide sequence chosen from SEQ ID NO: 6, SEQ ID NO: 7, SEQ ID NO: 8, SEQ ID NO: 9, and SEQ ID NO: 10 and derivatives thereof.

In a related aspect, the invention relates to an expression vector which comprises a nucleotide encoding a bradykinin $B_1$ receptor having a sequence chosen from SEQ ID NO: 1, SEQ ID NO: 2, SEQ ID NO: 3, SEQ ID NO: 4, and SEQ ID NO: 5 and functional derivatives thereof or a nucleotide having a sequence chosen from SEQ ID NO: 6, SEQ ID NO: 7, SEQ ID NO: 8, SEQ ID NO: 9, and SEQ ID NO: 10 and derivatives thereof.

In yet another aspect, the invention relates to a recombinant cell comprising the expression vector described above and capable of expressing a bradykinin $B_1$ receptor from the expression vector, as well as a method for producing such a cell. The method comprises transfecting a suitable host cell with the expression vectors described above and maintaining the host cells under conditions in which the bradykinin $B_1$ gene is expressed.

In a related aspect, the present invention relates to a method of identifying a compound that modulates bradykinin $B_1$ receptor activity. The method comprises contacting the test compound with a bradykinin $B_1$ receptor comprising an amino acid sequence chosen from SEQ ID NO: 1, SEQ ID NO: 2, SEQ ID NO: 3, SEQ ID NO: 4, and SEQ ID NO: 5 and functional derivatives thereof; and measuring an effect of the compound on the receptor. The bradykinin $B_1$ receptor may be expressed by a recombinant host cell. The effect to be measured may be a binding effect, for example, the displacement of a peptidic or non-peptidic ligand or a native ligand, such as, des-$Arg^{10}$-kallidin, from the receptor.

In yet another aspect, the invention relates to a method of identifying an animal model for testing compounds with potential efficacy as bradykinin $B_1$ receptor modulators. The method comprises contacting a test compound with a panel of bradykinin $B_1$ receptors from several species; measuring an effect of the compound on the receptors; and then selecting an animal model for further study of the compound's efficacy wherein the animal selected represents a species having a bradykinin $B_1$ receptor that exhibits the desired effect when contacted with the test compound. In this method, the bradykinin $B_1$ receptors comprise proteins having amino acid sequences chosen from SEQ ID NO: 1, SEQ ID NO: 2, SEQ ID NO: 3, SEQ ID NO: 4, and SEQ ID NO: 5 and functional derivatives thereof. Alternatively, the bradykinin $B_1$ receptors are encoded by nucleotides having sequences chosen from SEQ ID NO: 6, SEQ ID NO: 7, SEQ ID NO: 8, SEQ ID NO: 9, and SEQ ID NO: 10 and derivatives thereof.

In yet another aspect, the invention relates to a method of identifying a compound having dual specificity to modulate bradykinin $B_1$ receptor activity in two different species comprising contacting the compound with a bradykinin $B_1$ receptor from a first species; measuring an effect of the compound on said first receptor; contacting the compound with a bradykinin $B_1$ receptor from a second species; measuring an effect of said compound on said second receptor; and, based on these measurements, determining whether the compound is equipotent for both receptors. In one embodiment, the method enables one to identify a compound having dual specificity to modulate bradykinin $B_1$ receptor activity in a primate and non-primate.

BRIEF DESCRIPTION OF THE DRAWINGS

FIGS. 1a–b depict the amino acid sequence of bradykinin $B_1$ receptors from five mammalian species.

FIG. 3 shows the percent identity for all combinations of the cloned $B_1$ receptors.

FIG. 6 shows the $K_D$ and $K_I$ values at the different orthologues. Table a of FIG. 6 shows the $K_D$ values for [$^3$H]-des-Arg$^{10}$-Kallidin at each of the cloned receptors. Table b of FIG. 6 shows the $K_I$ values for the peptides and small molecules at the cloned receptors.

DETAILED DESCRIPTION OF THE INVENTION

Figure 2A:
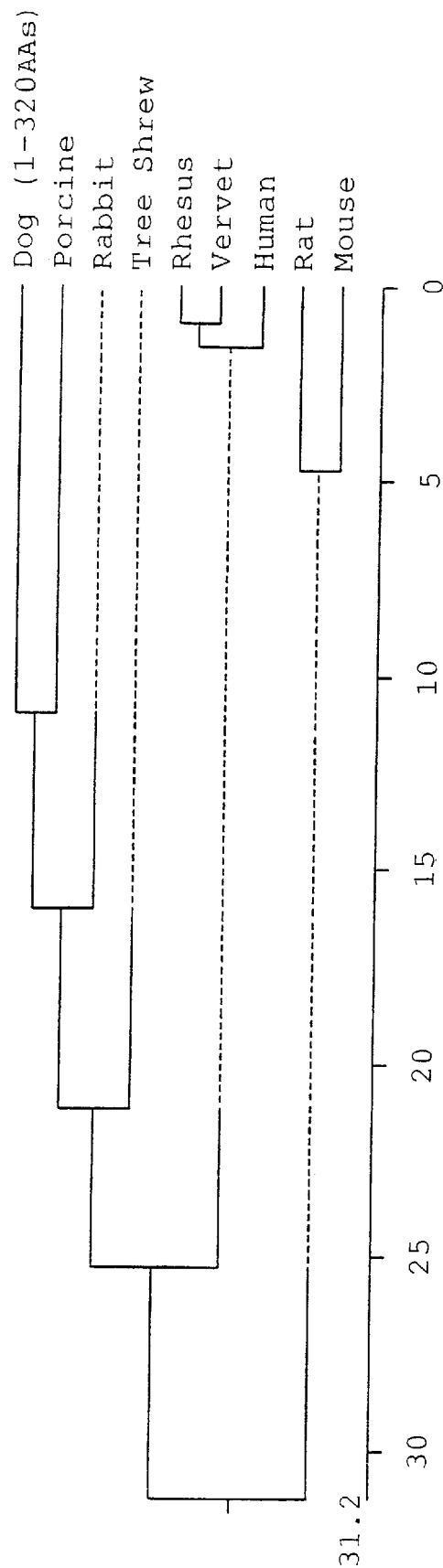
FIGS. 2a and 2b are schematics depicting putative phylogenetic relatedness of the $B_1$ receptor orthologues.

All patent applications, patents and literature references cited herein are hereby incorporated by reference in their entirety.

The invention encompasses bradykinin $B_1$ receptor nucleotides, bradykinin $B_1$ receptor proteins and peptides, as well as use of these molecules to identify modulators of bradykinin $B_1$ receptor activity. Modulators identified in this process, including but not limited to agonists, antagonists, suppressors and inducers, may be useful as therapeutic agents in the treatment of pain and inflammation.

In practicing the present invention, many conventional techniques in molecular biology, microbiology, and recombinant DNA are used. Such techniques are well known and are explained in, for example, Sambrook et al., 1984, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); Nucleic Acid Hybridization, 1985, (Hames and Higgins, eds.); *Transcription and Translation*, 1984 (Hames and Higgins, eds.); *Animal Cell Culture*, 1986 (R. I. Freshney ed.); *Immobilized Cells and Enzymes*, 1986, (IRL Press); Perbas, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively); *Current Protocols in Molecular Biology*, John Wiley & Sons, Inc. (1994), and all more recent editions of these publications.

Definitions

In the description that follows certain conventions will be followed as regards the usage of terminology:

The term "expression" refers to the transcription and translation of a structural gene (coding sequence) so that a protein (i.e. expression product) having the biological activity of the bradykinin $B_1$ receptor is synthesized. It is understood that post-translational modifications may remove portions of the polypeptide which are not essential and that glycosylation and other post-translational modifications may also occur.

The term "transfection," as used herein, refers to the introduction of DNA into a host cell by any means, and includes, without limitation, transfection of episomes and other circular DNA forms. The expression vector may be introduced into host cells via any one of a number of techniques including but not limited to viral infection, transformation, transfection, lipofection, protoplast fusion, and electroporation.

The term "derivative(s)" refers to a protein, peptide, polypeptide or polynucleotide which is derived from one of SEQ ID NOs. 1–12. It is intended to encompass polypeptides or peptides corresponding to functional domains (for example, one or more extracellular domains, one or more transmembrane domains, one or more cytoplasmic domains) of the bradykinin $B_1$ receptor, a mutated, truncated or deleted bradykinin $B_1$ receptor (that is, a receptor with one or more functional domains or portions thereof deleted), fusion proteins, and chimeras and fragments thereof. The invention also encompasses nucleotide sequences encoding such products, as well as expression vectors containing these nucleotides and capable of producing such bradykinin $B_1$ receptor products. A "functional derivative" is a derivative which retains the activity of the native molecule.

Because the genetic code is degenerate, more than one codon may be used to encode a particular amino acid, and therefore, the amino acid sequence can be encoded by any set of similar DNA oligonucleotides. With respect to nucleotides, therefore, the term "derivative(s)" is also intended to encompass those DNA sequences which contain alternative codons which code for the eventual translation of the identical amino acid.

Nucleotides and Proteins

Figure 1A:
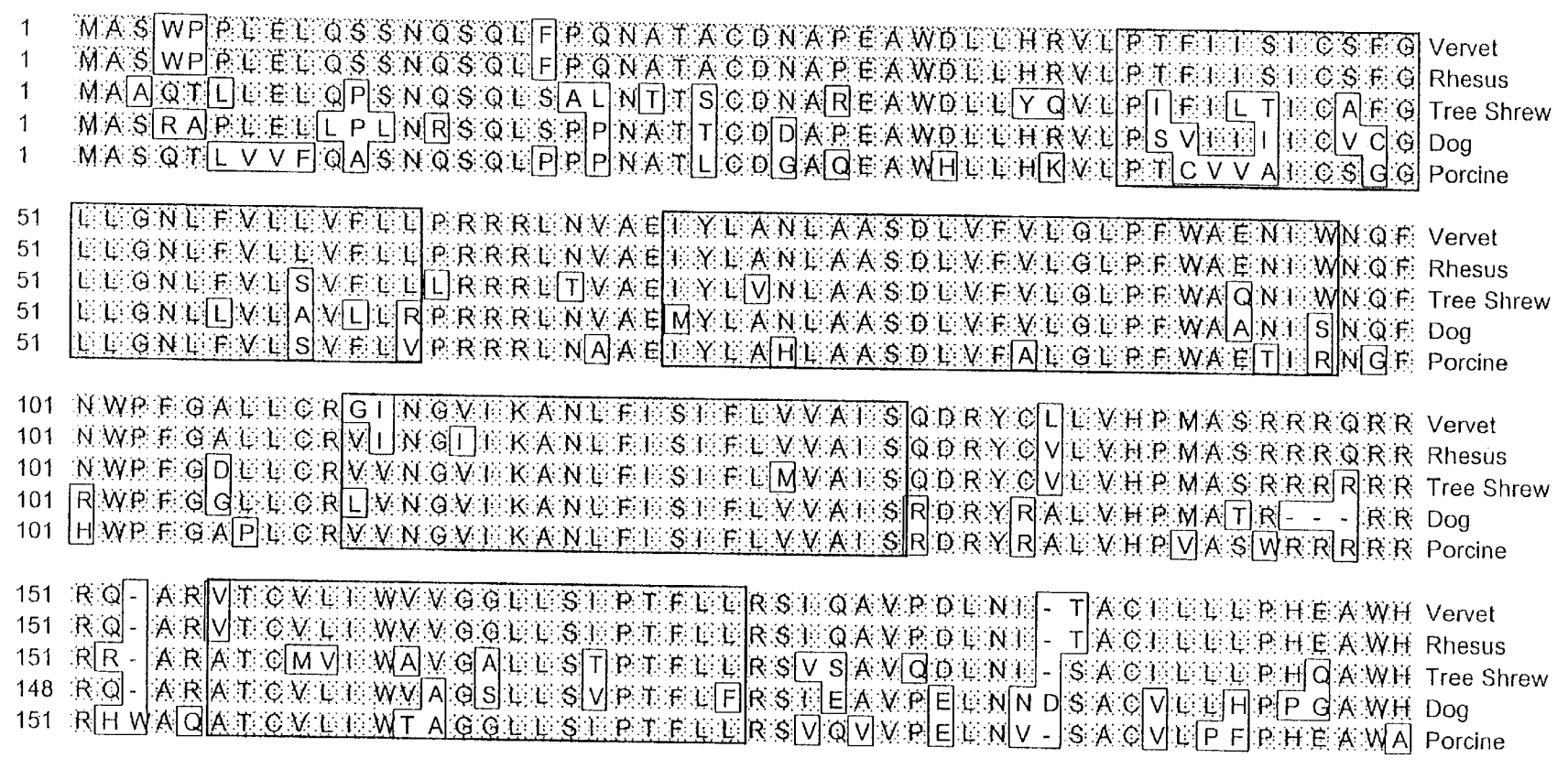
Figure 1B:
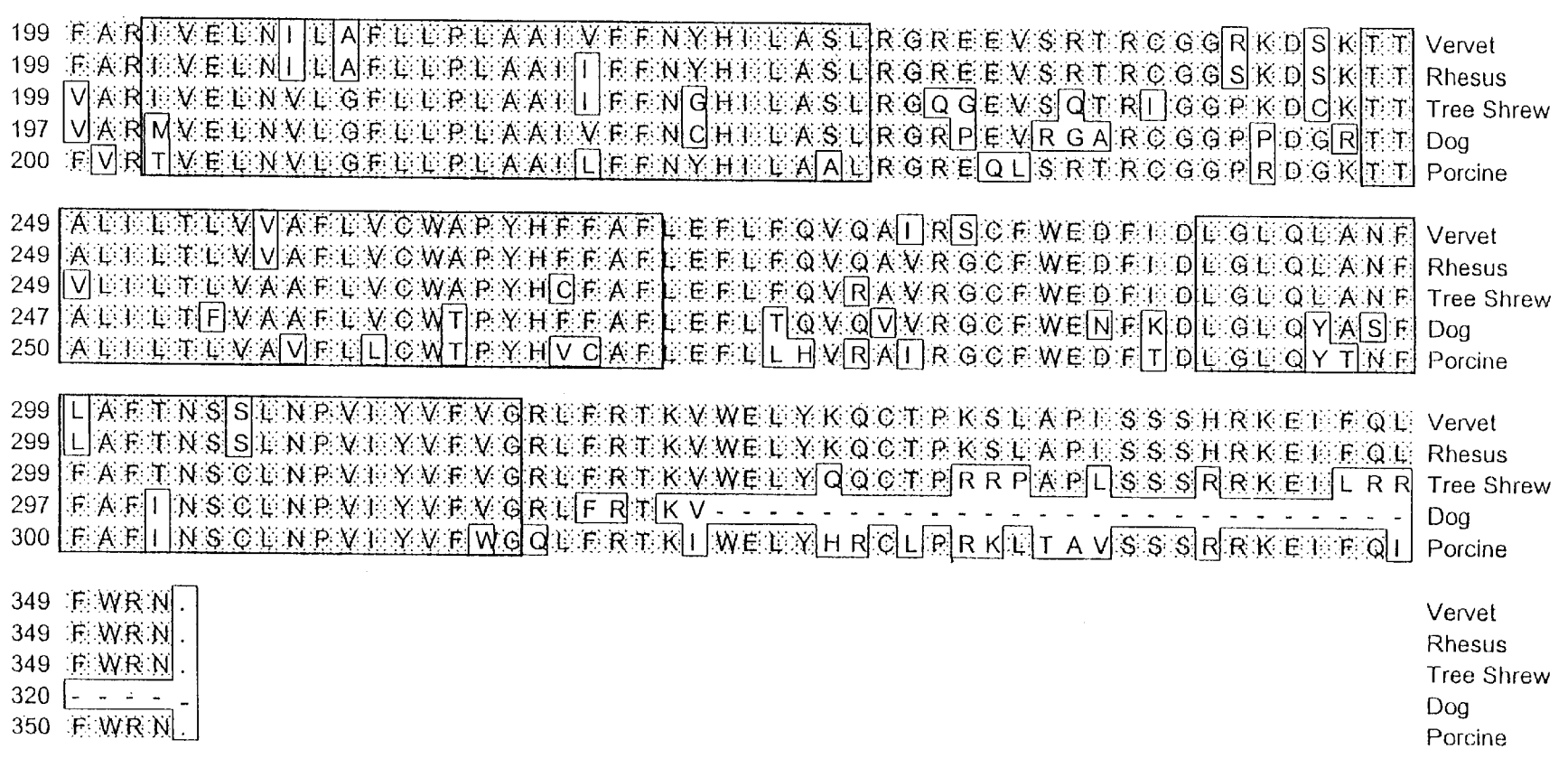

The bradykinin $B_1$ receptor genes from five mammalian species, namely, vervet monkey (SEQ ID NO. 7), rhesus macaque (SEQ ID NO. 8), tree shrew (SEQ ID NO. 9), pig (SEQ ID NO. 12), and dog (SEQ ID NO. 10), have been cloned and characterized. The deduced amino acid sequences for bradykinin $B_1$ receptors from vervet (SEQ ID NO. 1), rhesus (SEQ ID NO. 2), tree shrew (SEQ ID NO. 3), pig (SEQ ID NO. 6), and dog (SEQ ID NO. 4), are shown in FIG. 1. Additionally, the amino acid sequence for a dog/human chimeric receptor (SEQ ID NO. 5) and a nucleic acid sequence which encodes the chimera (SEQ ID NO. 11) is disclosed.

The bradykinin $B_1$ receptor polypeptides of the present invention include the polypeptides of SEQ ID NOs: 1–6; and a polypeptide comprising an amino acid sequence which has at least 80% identity to one of SEQ ID NOs: 1–6 over its entire length, and still more preferably at least 90% identity, and even still more preferably at least 95% identity to one of SEQ ID NOs: 1–6. Furthermore, those with at least 97–99% are highly preferred. Preferably, bradykinin $B_1$ receptor polypeptides exhibit at least one biological activity of the receptor.

The bradykinin $B_1$ receptor polypeptides may be in the form of the "mature" protein or may be a part of a larger protein such as a fusion protein. It is often advantageous to include an additional amino acid sequence which contains secretory or leader sequences, prosequences, sequences which aid in purification such as multiple histidine residues, or an additional sequence for stability during recombinant production.

The invention also encompasses variant proteins that are functionally equivalent to the bradykinin $B_1$ receptors encoded by the nucleotide sequences described above, as judged by any of a number of criteria, including but not limited to the ability to bind ligands known to interact at the $B_1$ receptor, the binding affinity for ligand, the resulting biological effect of ligand binding, for example, phosphatidyl inositol hydrolysis, release of intracellular $Ca^{++}$, or arachidonic acid release mediated by des-Arg$^{10}$kallidin or des-Arg$^9$bradykinin and signal transduction molecules, such as diacyl glycerol and protein kinase C that cause a change in cellular metabolism, (e.g., ion flux, tyrosine phosphorylation).

Such functionally equivalent bradykinin $B_1$ receptor proteins include but are not limited to those proteins containing additions, deletions or substitutions of amino acid residues within the amino acid sequence encoded by the bradykinin $B_1$ receptor nucleotide sequences described, but which result in a silent change, thus producing a functionally equivalent gene product. Amino acid substitutions may be made on the basis of similarity in polarity, charge, solubility, size, hydrophobicity, hydrophilicity, and/or the amphipathic nature of the residues involved. For example, nonpolar (hydrophobic) neutral amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. While random mutations can be made to bradykinin $B_1$ receptor DNA (using random mutagenesis techniques well known to those skilled in the art) and the resulting mutant bradykinin $B_1$ receptor tested for activity, site-directed mutations of the bradykinin $B_1$ receptor coding sequence can be engineered (using site-directed mutagenesis techniques well known to those skilled in the art) to generate mutant bradykinin $B_1$ receptors with altered function, e.g., lower binding affinity for ligand and/or decreased signal transduction capacity.

Fragments of the bradykinin $B_1$ receptor polypeptides are also included in the invention. A fragment is a polypeptide having an amino acid sequence that entirely is the same as part, but not all, of the amino acid sequence of the aforementioned bradykinin $B_1$ receptor polypeptides. As with bradykinin $B_1$ receptor polypeptides, fragments may be "free-standing," or comprised within a larger polypeptide of which they form a part or region, most preferably as a single continuous region.

Preferred fragments include, for example, truncation polypeptides having the amino acid sequence of bradykinin $B_1$ receptor polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding regions, and high antigenic index regions. Other preferred fragments are biologically active fragments. Biologically active fragments are those that mediate or inhibit receptor activity, including those with a similar activity or an improved activity, or with a decreased undesirable activity. Also included are those fragments that are antigenic or immunogenic.

The bradykinin $B_1$ receptor polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Bradykinin $B_1$ receptor polynucleotides include isolated polynucleotides which encode the bradykinin $B_1$ receptor polypeptides and derivatives thereof, and polynucleotides closely related thereto. More specifically, bradykinin $B_1$ receptor polynucleotides of the invention include polynucleotides comprising a nucleotide sequence selected from SEQ ID NOs: 7–12, encoding a bradykinin $B_1$ receptor polypeptide of SEQ ID NOs: 1–6. Bradykinin $B_1$ receptor polynucleotides further include a polynucleotide comprising a nucleotide sequence that has at least 80% identity to a nucleotide sequence encoding one of the bradykinin $B_1$ receptor polypeptides of SEQ ID NOs: 1–6 over its entire length, and a polynucleotide that is at least 80% identical to one of those set forth in SEQ ID NOs: 7–12 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included are nucleotide sequences which have sufficient identity to a nucleotide sequence selected from SEQ ID NOs: 7–12 to hybridize under conditions useable for amplification or for use as a probe or marker. The invention also provides polynucleotides which are complementary to such bradykinin $B_1$ receptor polynucleotides.

The nucleotide sequences encoding the bradykinin $B_1$ receptor polypeptides of SEQ ID Nos: 1–6 may be identical to the polypeptide-encoding sequences of SEQ ID NOs: 7–12), or may be any sequence, which as a result of the redundancy (degeneracy) of the genetic code, also encodes the polypeptides of SEQ ID Nos: 1–6.

When the polynucleotides of the invention are used for the recombinant production of bradykinin $B_1$ receptor polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding bradykinin $B_1$ receptor variants comprising the amino acid sequence of a bradykinin $B_1$ receptor polypeptide selected from SEQ ID NOs: 1–6 in which several, 5–10, 1–5, 1–3, 1–2 or 1 amino acid residues are substituted, deleted or added, in any combination. The nucleotide sequences used as probes to identify the bradykinin $B_1$ receptors of the present invention are shown in SEQ ID NOs: 7–12 and encode the amino acid sequences of SEQ ID NOs: 1–6.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO: 7–12 or a fragment thereof may be used as hybridization probes for cDNA and genomic DNA, to isolate full-length cDNAs and genomic clones encoding bradykinin $B_1$ receptor and to isolate cDNA and genomic clones of other genes that have a high sequence similarity to the bradykinin $B_1$ receptor gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Isolation of DNA

DNA encoding a bradykinin B receptor, in accordance with the instant invention, may be obtained, by chemical synthesis, by screening reverse transcripts of mRNA or cDNA from appropriate cells, for example, lung fibroblasts, aortic smooth muscle, mesangial cells, renal cells, intestinal smooth muscle cells or cell line cultures of the appropriate species, by screening genomic libraries, or by combinations of these procedures. Screening of mRNA, cDNA or genomic DNA may be carried out with oligonucleotide probes generated from the nucleic acid sequence information of the bradykinin $B_1$ receptors disclosed herein.

For purposes of practicing the present invention, DNA encoding a bradykinin $B_1$ receptor of a particular species can be obtained from any cDNA library prepared from tissue from the species believed to possess the receptor mRNA and to express it at a detectable level. The bradykinin $B_1$ receptors can also be obtained from genomic libraries for the desired species.

Identification of bradykinin $B_1$ receptor DNA is most conveniently accomplished by probing an appropriate cDNA or genomic library with labeled oligonucleotide sequences selected from known bradykinin $B_1$ receptor sequences. For example, in one embodiment, a method for obtaining a polynucleotide encoding a bradykinin $B_1$ receptor polypeptide comprises the steps of screening an appropriate library under stringent hybridization conditions with a labeled probe having a sequence selected from SEQ ID NOs: 7–12 or a fragment thereof, and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C.

An alternative means to isolate the gene encoding a bradykinin $B_1$ receptor is to use polymerase chain reaction (PCR) methodology as described in Sambrook et al., *Molecular Cloning: A Laboratory Manual*, second edition, Cold Spring Harbor Laboratory Press, Cold Spring Harbor, N.Y.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *Basic Methods In Molecular Biology* (1986) and Sambrook et al., *Molecular Cloning: A Laboratory Manual*, 2nd Ed., Cold Spring Harbor Laboratory Press, Cold Spring Harbor, N.Y. (1989). Such methods include calcium phosphate transfection, DEAE-dextran mediated transfection, microinjection, cationic lipid-mediated transfection, electroporation, transduction, scrape loading, ballistic introduction or infection.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *Molecular Cloning, A Laboratory Manual* (supra).

Representative examples of appropriate hosts include bacterial cells, such as *E. coli*, Streptomyces and Bacillus subtilis cells; fungal cells, such as yeast cells and Aspergillus cells; insect cells such as Drosophila S2 and Spodoptera Sf9 cells; animal cells and plant cells. One of skill in the art will recognize that different host cells have characteristic and specific mechanisms for the post-translational processing and modification of proteins and gene products. Host cells suitable for expression of the inserted bradykinin receptor sequences of the present invention are those having the capability to effect such post-translational modifications as necessary to produce a functional bradykinin receptor. Suitable mammalian host cells include but are not limited to CHO, VERO, BHK, HeLa, COS, MDCK, HEK 293, 3T3, W138.

When using an episomally-based plasmid such as the pE3hyg episomal expression vector described herein, any eukaryotic cells which support stable replication of the plasmids may be used in practicing the invention. Non-limiting examples of host cells for use in the present invention include HEK 293 cells (American Type Culture Collection, Manassas, Va. (ATCC) Deposit Number CRL-1573), CV1EBNA cells (ATCC CRL10478), Hela cells, D98/Raji cells, 293EBNA (also referred to herein as "293E cells") available from Invitrogen, Cat. No. R62007, CV1 cells (ATCC Cat. No. CCL70) and 143B cells (ATCC Cat. No. CRL-8303).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the bradykinin $B_1$ receptor polypeptide is to be expressed for use in screening assays, generally, it is preferred that the polypeptide be produced at the surface of the cell. In this event, the cells may be harvested prior to use in the screening assay. If bradykinin $B_1$ receptor polypeptide is secreted into the medium, the medium can be recovered in order to recover and purify the polypeptide; if produced intracellularly, the cells must first be lysed before the polypeptide is recovered.

Bradykinin $B_1$ receptor polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

The bradykinin $B_1$ receptors of the present invention may be employed in a screening process for compounds which bind the receptor and which activate (agonists) or inhibit activation (antagonists) of the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics.

Bradykinin $B_1$ receptor polypeptides are responsible for many biological functions, including many pathologies. Accordingly, it is desirable to find compounds and drugs which stimulate the receptor on the one hand, or which can inhibit the function of the receptor on the other hand.

In general, such screening procedures involve producing appropriate cells which express the receptor polypeptide of the present invention on the surface thereof. Such cells include cells from mammals, yeast, Drosophila or E. coli. Cells expressing the receptor (or cell membrane containing the expressed receptor) are then contacted with a test compound to observe binding, or stimulation or inhibition of a functional response.

One screening technique includes the use of cells which express receptor of this invention (for example, 293E cells stably transfected with an episome containing one of the polynucleotides of the invention) in a system which measures receptor binding, or extracellular pH or intracellular calcium changes caused by receptor activation. In this technique, compounds may be contacted with cells expressing the receptor polypeptide of the present invention. Receptor binding or a second messenger response, e.g., signal transduction, pH changes, or changes in calcium level, is then measured to determine whether the test compound activates or inhibits the receptor, or inhibits agonist-induced activation of the receptor.

Another method involves screening for receptor inhibitors/activators by determining inhibition or stimulation of receptor-mediated cAMP, inositol phosphate and/or adenylate cyclase accumulation. Such a method involves transfecting a eukaryotic cell with the receptor of this invention to express the receptor on the cell surface. The cell bearing the receptor is then exposed to potential agonists, antagonists or inverse agonists in the presence and absence of ligand. The amount of cAMP or inositol phosphate accumulation is then measured. If a potential antagonist or inverse agonist binds the receptor, and thus inhibits receptor binding by native ligand or other agonist, the levels of receptor-mediated cAMP, inositol phosphate or adenylate cyclase activity will be reduced. Conversely, if a potential agonist binds the receptor, thereby activating the receptor, the levels of receptor-mediated cAMP, inositol phosphate or adenylate cyclase are increased.

The assays may simply test binding of a candidate compound wherein adherence to the receptor, or to cells bearing the receptor, is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential bradykinin $B_1$ receptor inhibitors include antagonists, inverse agonists, antibodies or, in some cases, oligonucleotides or proteins which are closely related to the ligand of the bradykinin $B_1$ receptor e.g., peptides or small molecules which bind to the receptor but do not elicit a response, so that the activity of the receptor is prevented.

As discussed earlier, in more recent paradigms of drug discovery, screening efforts are typically conducted on cloned human targets but resulting properties of lead candidates are sometimes complicated by lack of efficacy in animal models of choice. Identification of the nucleotides and proteins of the present invention provide a unique opportunity for identifying an animal model for testing compounds which have potential efficacy as bradykinin $B_1$ receptor modulators. The method comprises contacting the test compound with a panel of bradykinin $B_1$ receptors from at least two species; measuring an effect of the compound such as receptor binding or a second messenger response on the receptors; and finally, selecting an animal model wherein the animal chosen represents a species having a bradykinin $B_1$ receptor that exhibits the desired effect when contacted with the test compound. In one embodiment, one of the species is a primate and the other is a non-primate.

EXAMPLES

Tree shrew (Tupaia minor) genomic DNA was obtained from Dr. Marc Allard (Dept. Of Biological Sciences, George Washington University, Washington, D.C.) Dog, pig, rabbit, human and rat genomic DNAs were purchased from Clonetech (Palo Alto, Calif.). Genomic DNA from Vervet monkey (Cercopithecus pygerythrus) was isolated from a liver biopsy specimen obtained from Caribbean Primates Ltd. (St. Kitts, West Indies). Genomic DNA from rhesus macaque (Macaca mulatta) was purchased from Clonetech (Palo Alto, Calif.).

Oligonucleotides to amplify the coding regions for the $B_1$ homologue from the human, rabbit and rat were designed according to published sequences and contain appropriate Kozak consensus sequences for subsequent expression (Table 1).

TABLE 1

Oligonucleotides used for isolation of B1 gene

| | | | Seq. ID No. |
|---|---|---|---|
| Universal | sense | tgtycmkkycrrgtcactgtgsatggc | 13 |
| | antisense | gctgytttaattccgccagaa | 14 |
| Human | sense | ggactagtaccaccatggcatcatcctggc | 15 |
| | antisense | gcgtcgacggttcaatgctgttttaattccgcc | 16 |

TABLE 1-continued

Oligonucleotides used for isolation of B1 gene

| | | | Seq. ID No. |
|---|---|---|---|
| Rabbit | sense | gcatgccaccatggcgtccgaggtcttgttg | 17 |
| | antisense | tgacttataaagtccccagaaccctg | 18 |
| Rat | sense | gcatgccaccatggcgtccgaggtcttgttg | 17 |
| | antisense | tgacttataaagtccccagaaccctg | 18 |
| Macaque | sense | ataggtaccgccaccatggcatcctggccccctctagag | 19 |
| | antisense | gcgctcgaggctgttttaattccgccagaa | 20 |
| Vervet | sense | ataggtaccgccaccatggcatcctggccccctctagag | 19 |
| | antisense | gcgctcgaggctgttttaattccgccagaa | 20 |
| Tree shrew | sense | ataggtaccgccaccatggcagcccagacactcctg | 21 |
| | antisense | gcgctcgagttaattccgccagaaamgcc | 22 |
| Pig | sense | ataggtaccgccaccatggcctcccagaccctcgtg | 23 |
| | antisense | gcgctcgaggctgttttaattccgccagaa | 24 |
| Dog | sense | ataggtaccgccaccatggcatcgcgggccccctg | 25 |
| | antisense | raccytggtcytrargagccggcc | 26 |

Polymerase chain reaction (PCR) was used to amplify the coding sequences from vervet monkey (Cercopithecus pygerythrus), rhesus macaque (Macaca mulatta), pig, and tree shrew (Tupaia minor). Degenerate oligonucleotides were designed to the consensus derived from human, rodent and lapine sequences from nt −24 to nt +5 (universal sense oligonucleotide, Table 1) and to the region across or near the stop codon (antisense). The resulting PCR amplicons were sequenced directly. Explicit oligos based on the PCR amplicon sequences were used to re-amplify from corresponding genomic DNAs. PCR products were digested with Kpn I and Xho I, and cloned into the corresponding sites of the episomal expression vector pE3hyg (Horlick et al., Gene 243(1–2) pp. 187–194, 2000).

Additionally, a canine/human chimeric bradykinin $B_1$ receptor comprising amino acids 1 to 315 of the canine sequence and amino acids 319–353 of human bradykinin $B_1$ receptor was generated. Any number of chimeric molecules, for example, a chimera comprising amino acids 1–320 of the canine sequence and amino acids 324–353 of the human sequence can be used.

For the chimera, a 150 bp fragment corresponding to human $B_1$ amino acids 316 to 354 was PCR amplified with the sense oligo, 5'-GGCCGGCTCTTCAGGACCAAGGTC-3' (SEQ ID NO. 24) and the antisense oligo used for Rhesus, 5'-GCGCTCGAGGCTGTTTTAATTCCGCCAGAA-3' (SEQ. ID. NO. 17). The coding region for the first 320 codons of canine $B_1$ was successfully PCR amplified using the degenerate universal and dog antisense oligos (Table 1). Sequence information from this amplicon was used to make an explicit dog sense oligo (Table 1). PCR of the dog genomic DNA with this oligo and the original degenerate antisense oligo, raccytggtcytrargagccggcc (SEQ. ID. NO. 22), resulted in a fragment of 960 bp. The 960 bp partial dog $B_1$ PCR product and the 150 bp human $B_1$ PCR product were combined as the template for a second round of PCR amplification. The dog sense and the rhesus antisense oligos were used to create a chimera in this second round of PCR. The resulting 1.1 Kb PCR product was cleaved with KpnI and XhoI, and then cloned into the corresponding sites of the pE3-Hyg vector as described below.

It has been shown previously that the carboxy terminal cytoplasmic domain does not appear to play a role in the ligand binding properties of the human B 1 receptor and therefore, the chimeric canine/human receptor described above were used in the experiments described below.

Clustal sequence alignments were performed using Megalign 4.01 from DNASTAR, Inc. (Madison, Wis.). Amino acid sequence alignments, phylogenetic relationships and pairwise comparison of amino acid identities were performed using Lasergene software (DNAStar, Inc. Madison, Wis.).

Host cells, 293-EBNA (293E)(Invitrogen, Carlsbad, Calif.) were transfected as follows with an episomal vector containing a bradykinin $B_1$ receptor nucleotide to be expressed. 293E cells were grown in Dulbecco's Modified Eagles Medium (DMEM) (Life Technologies, Gaithersburg, Md.) supplemented with 10% fetal bovine serum, 5 mM Glutamax II (Life Technologies, Gaithersburg, Md.), 100U/ml penicillin, and 100 $\mu$g/ml of streptomycin. The cells were plated in T75 flasks at a density of $2\times10^6$ cells/ml in growth media and incubated overnight. Transfection of the cells was by the calcium precipitation method (Sambrook et al. in Molecular Cloning: A Laboratory Manual, 2nd edition) using a total of 5 $\mu$g of DNA. The precipitate was added to the cells and then incubated for 6–18 hours. Following this incubation the cells were washed once with growth media (about 5 ml) and then fresh media was added (about 10 ml) and the cells incubated for an additional 24 hours. The cells were then sub-cultured 1:10 in selection media, growth media supplemented with an antibiotic to which the successfully transfected cell has acquired resistance.

Membrane Preparation

Membrane preparations for use in accordance with the methods of the present invention were generated as follows. 293E cells expressing $B_1$ receptors were harvested and pelleted. Cells were washed once with PBS and once with a membrane buffer (for example, 10 mM HEPES pH 7.5, 1 $\mu$M phosphoramidon, 3 $\mu$M amastatin, 1 $\mu$M captopril, 2 $\mu$M dithiothreitol (DTT)). Cells were resuspended in membrane buffer and Dounce homogenized on ice 35 times. The membranes were collected by centrifugation at 15,000×g for 30 min. at 4° C. and resuspended in membrane buffer containing 0.2% bovine serum albumin (BSA) at a final concentration of approximately $5\times10^6$ cell equivalents per ml. Aliquots were flash frozen and stored at −80° C. Frozen aliquots were subsequently thawed, diluted, and sonicated on ice using a Branson Sonifier® 250 (4×15 sec, 40% output).

Prior to use in a binding assay, a membrane preparation is "calibrated" as described below to determine the amount of membrane preparation to be used. A frozen sample of a membrane preparation is thawed and the preparation diluted in assay buffer to obtain several different concentrations of membranes, for example, 1:5, 1:10, 1:20, 1:40 and so on. The diluted membrane preparation is sonicated in a bath style sonicator for 5 minutes at room temperature. Each dilution is plated in a 96-well plate, for example, with quintuplicate samples for binding of ligand and wells to evaluate non-specific binding in triplicate. The dilutions that yield approximately 200 cpm total counts are chosen for subsequent assays.

Binding Assays

The method of the present invention employs a binding assay such as the one described below. A suitable binding assay buffer for rat receptor binding consists of 10 mM TES pH 6.8, 1 mM EDTA, 1 $\mu$M Plummer's Inhibitor, 1 $\mu$M enalapril, and 10 $\mu$M thiorphan. The buffer for all other species consists of Hank's Buffered Saline Solution (HBSS), 10 mM HEPES pH 7.5, 1 mM 1,10-phenanthroline, and 140 mg/L bacitracin. Competitor compounds, peptide or small molecule, were resuspended in 100% dimethyl sulfoxide (DMSO) and diluted to a final concentration of 5% DMSO in the reaction mixture. Binding reactions were carried out in 96-well microtiter dishes, 100 μl reaction volume per well in the presence of 1.5 nM (rat) or 0.6 nM (all other species) [$^3$H]-des-Arg$^{10}$-kallidin ([$^3$H]-dAKd) (NEN, Boston, Mass.). Binding reactions were initially chilled on ice for 10 min. and then continued at 4° C. for 1 hour. Reaction mixtures were transferred to glass fiber filter-plates which had been pre-blocked with 0.3% polyethyleneimine (PEI) (Sigma, St. Louis, Mo.), and washed 6 times with ice cold 50 mM Tris pH 7.5. 50 μl of scintillation fluid was added to each well and plates were counted in a Wallac Microbeta® TriLux for 10 min. per well.

B$_1$ Orthologues from Five Mammalian Species

Figure 2B:
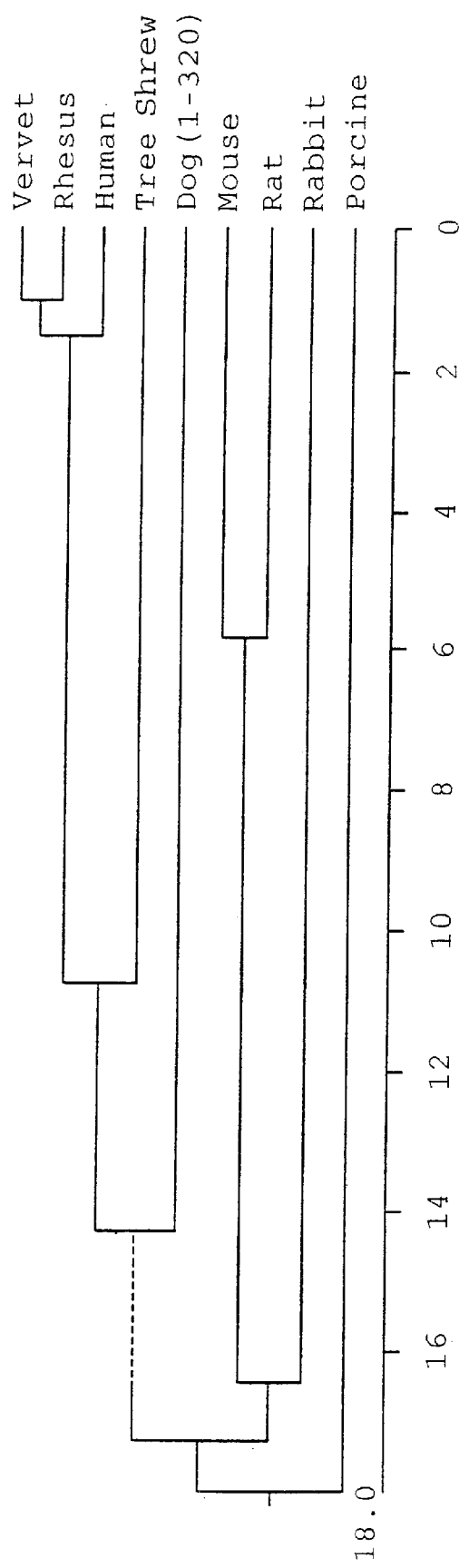

In order to assess the species-specificity profiles of potential small molecule antagonist molecules, the B$_1$ receptor coding regions from 5 mammalian species were cloned and characterized. Because the coding sequence for the B$_1$ gene is known to be contained within a single exon, the relevant sequences were obtained by performing PCR directly on genomic DNA obtained from each species. An alignment of the amino acid sequences derived from five mammalian species is shown in FIG. 1. A pairwise comparison of percent amino acid identity among the B$_1$ receptor orthologues (shown in FIG. 3) reveals that the sequences of the B$_1$ receptor orthologues appear to be somewhat less well evolutionarily conserved than many other G protein coupled receptors (GPCRs) and numerous amino acid changes are found scattered throughout the receptor sequences. A dendritic chart showing a putative evolutionary relationship among the sequences (FIG. 2) is consistent with current concepts and demonstrates that both primates are very closely related to the human sequence (96% identical). The next most closely related sequence to humans belongs to the tree shrew (80.5% identical). Tree shrews are mouse-to-rat sized animals in the order, Scandentia, and have been postulated to be among the closest relative to primates. Next in order of amino acid identity is the rabbit orthologue (77.1%) followed by dog (75.3%). Murine and porcine sequences show even less conservation.

Pharmacology of Peptidic Ligands at the B$_1$ Receptors

The pharmacological profile of the B$_1$ orthologues was assessed using four B$_1$ and B$_2$ peptidic ligands (FIGS. 5 & 6). The average dissociation constant (K$_D$) of dAkd appears to be of mostly the same magnitude at each of the animal orthologues, varying between 0.6 nM (human) and 1.3 nM (rabbit) to 4.2 nM (tree shrew) (FIG. 6a). The measured affinities are within the range of values reported in the literature for human and rabbit B$_1$ receptors. Inhibition constants (K$_I$) were calculated from IC$_{50}$ values generated by the four peptide ligands, dAKd, BK, [des-Arg$^{10}$] [Leu$^9$] kallidin (dALKd), and [des-Arg$^9$]BK (dABK) in the presence of 0.6 nM or 1.5 nM [$^3$H]-dAKd, as indicated in the materials and methods section above. These results are shown in FIG. 6b. Whereas BK is inactive and dAKd is approximately equipotent at all of the species homologues, the other two peptidic ligands exhibit significant differences in affinity among the various B$_1$ receptors. For example, dALKd is more than an order of magnitude weaker at the dog B$_1$ vs. the other B$_1$ receptors; dABk exhibits low nM potency at dog, inactive at human, tree shrew and rhesus macaque, and weakly active at rabbit and pig B$_1$.

Pharmacology of Non-peptidic Ligands at the B$_1$ Receptors.

Figure 4A:
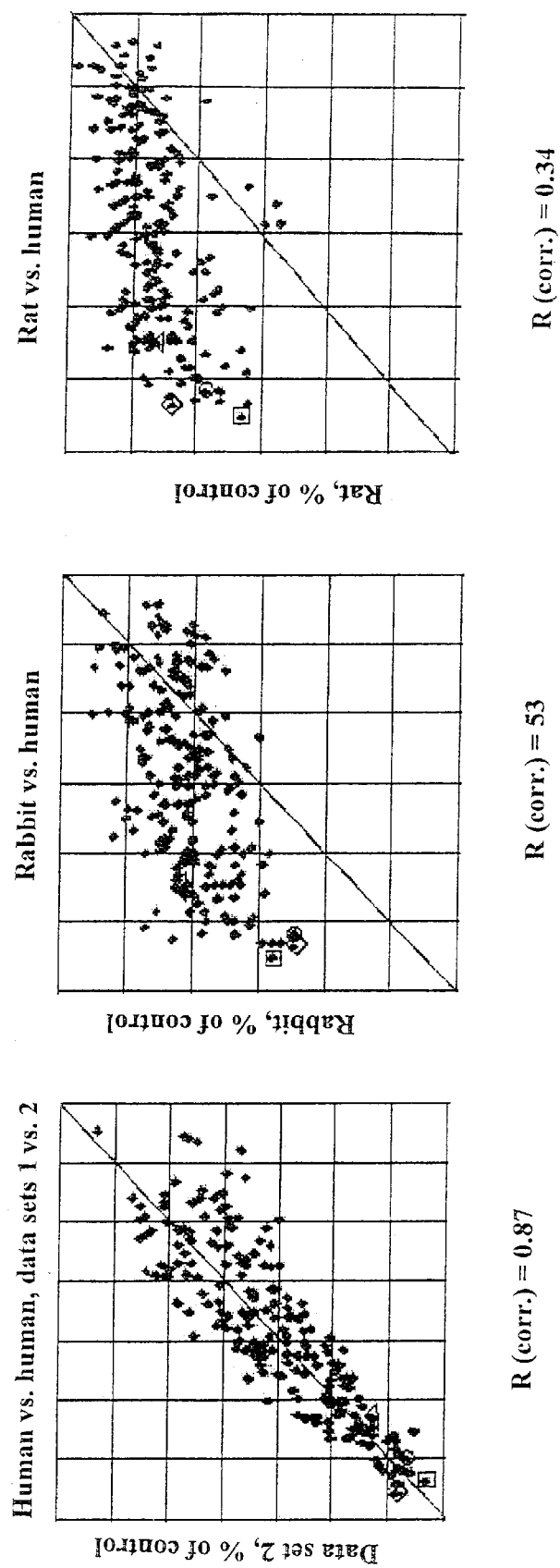
FIGS. 4a, 4b, and 4c show the results of comparison of activity of selected test compounds at animal vs. human $B_1$ receptor orthologues.
Figure 4B:
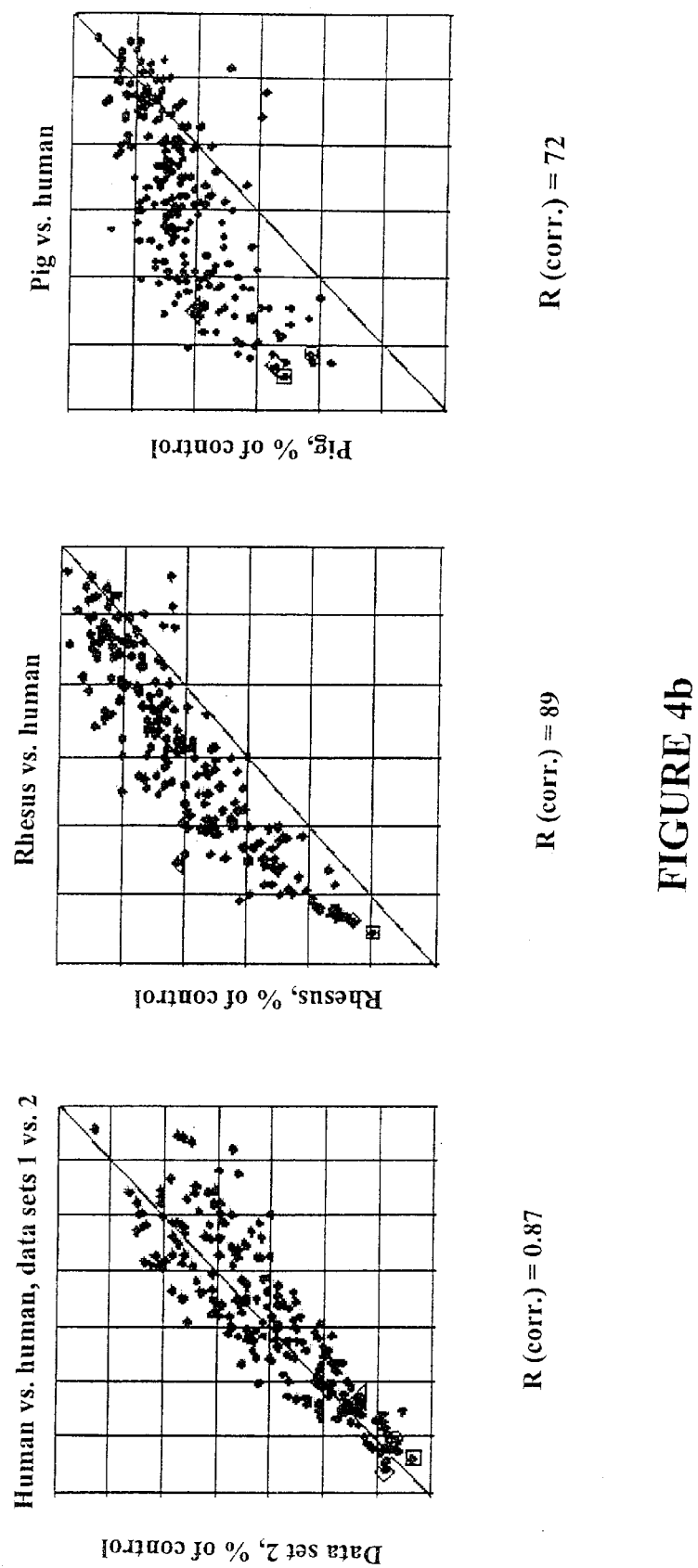
Figure 4C:
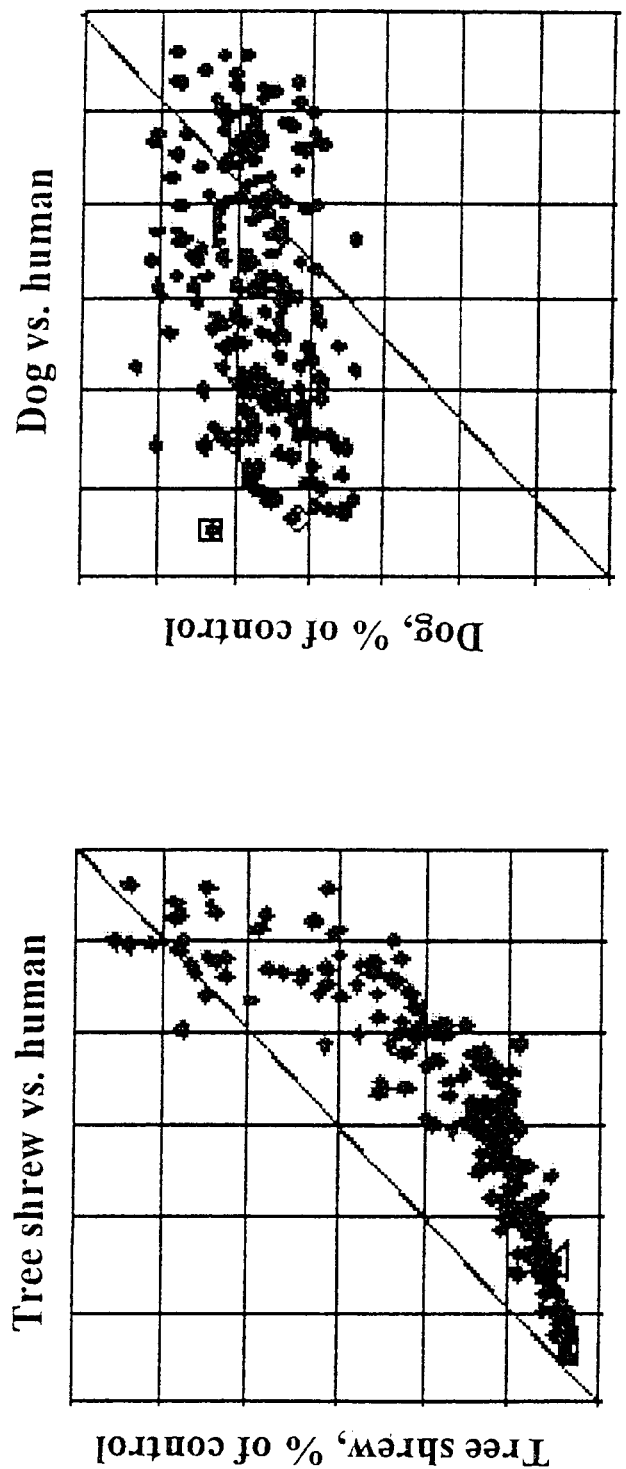

A subset of compounds that retain significant potency at most of the receptors was identified. Comparison of the activity of the compounds at animal vs. human B$_1$ receptor orthologues is shown in the scattergrams of FIGS. 4a–b. The solid line at 45° in each panel represents an isocline of equal potency. FIGS. 4a–b show two independent human data sets compared to each other, and species-to-human comparisons, as labeled at the top of each scattergram. The correlation coefficients of each pair of data sets is shown below each figure. Compounds were tested at 1 μM concentration at the rat B$_1$ receptor, and at 0.1 μM concentration at all other animal otrthologues. Displacement was tested in the presence of 1.5 nM [$^3$H]-dAKd for rat B$_1$, and 0.6 nM for all other B$_1$ receptors. Data points are marked as follow: □, PS978163; ◇, PS596668; ○, PS972282; Δ, PS309799. Conversely, a subset of compounds that exhibit considerable differences in specificity among the orthologues was also identified (data point for PS309799 shown enclosed by triangle, FIG. 4b). To verify the validity of the scattergram results, the potencies of these four non-peptide compounds were further assessed by ligand displacement assays at the B$_1$ orthologous receptors. A comparison of K$_I$S among the four compounds revealed dramatic differences in species specificity. Compound PS309799 showed the greatest variation of activity, ranging from low nM potency in tree shrew and human to inactive at dog and rabbit. PS596668 had a similar activity profile to PS309799 except it demonstrated potent activity at the rabbit B1. The remaining two compounds, PS972282 and PS978163, had measurable affinity constants at all six species, although PS978163 was considerably weaker at pig and dog.

Figure 5A:
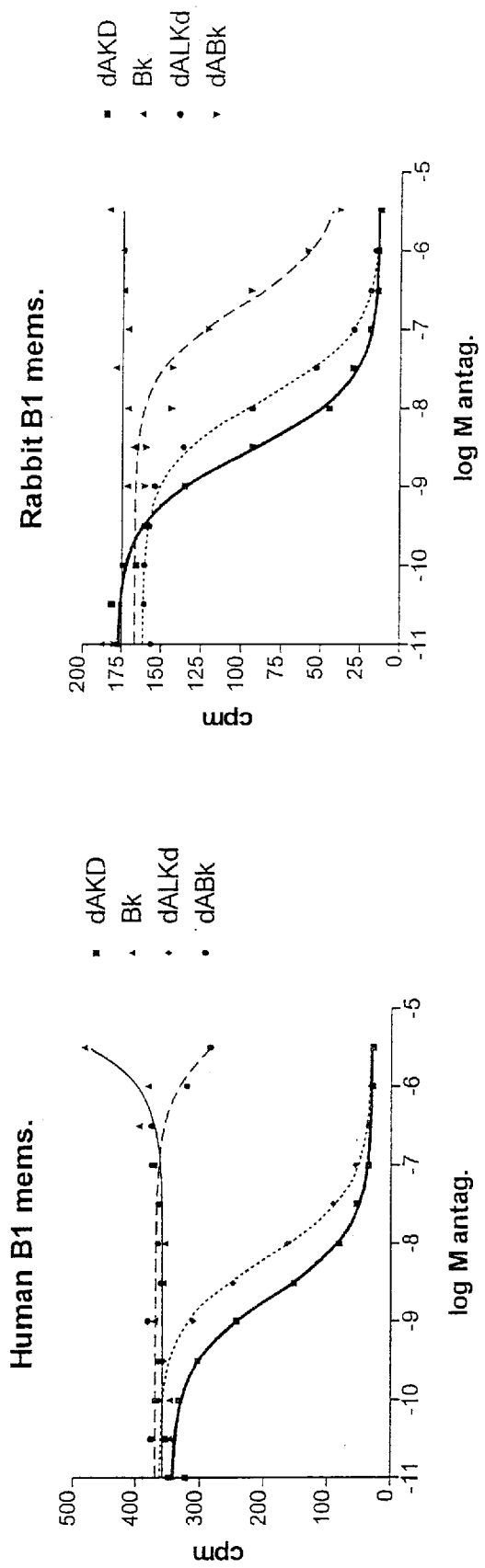
FIGS. 5a, 5b, 5c, 5d, 5e and 5f show the competition binding curves at each of the cloned receptors.
Figure 5B:
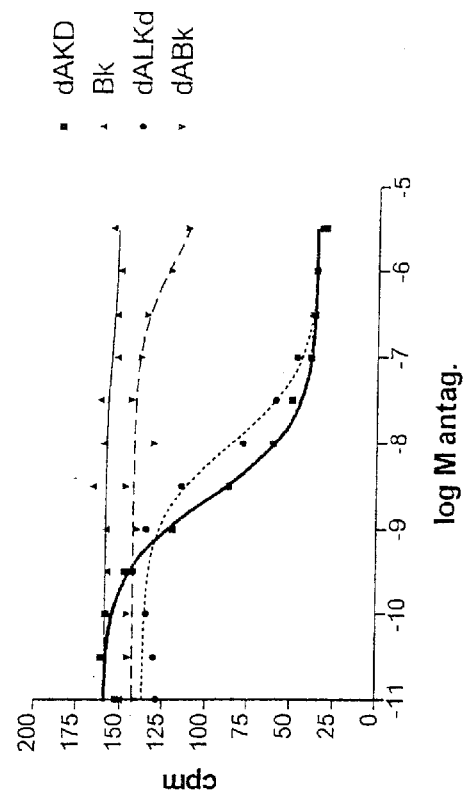
Figure 5B:
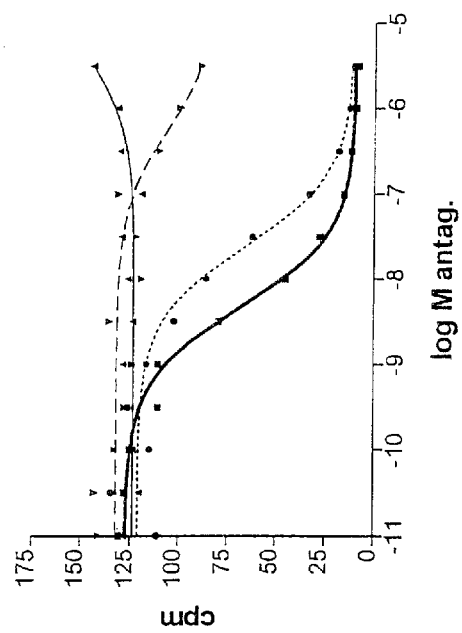
Figure 5C:
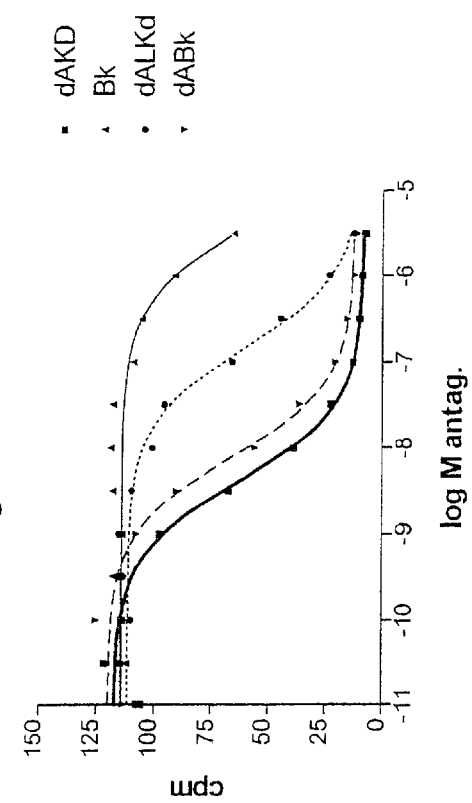
Figure 5C:
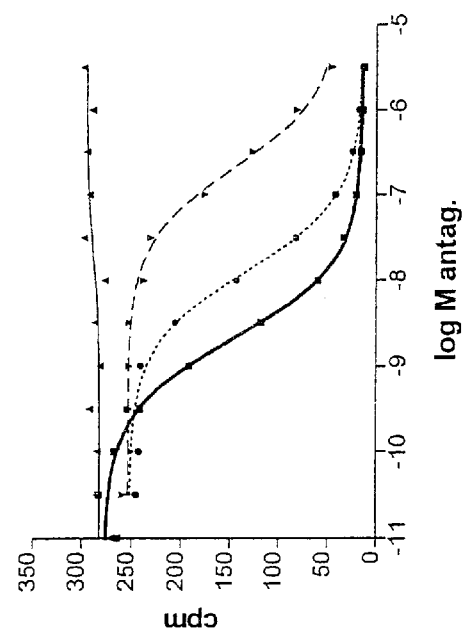
Figure 5D:
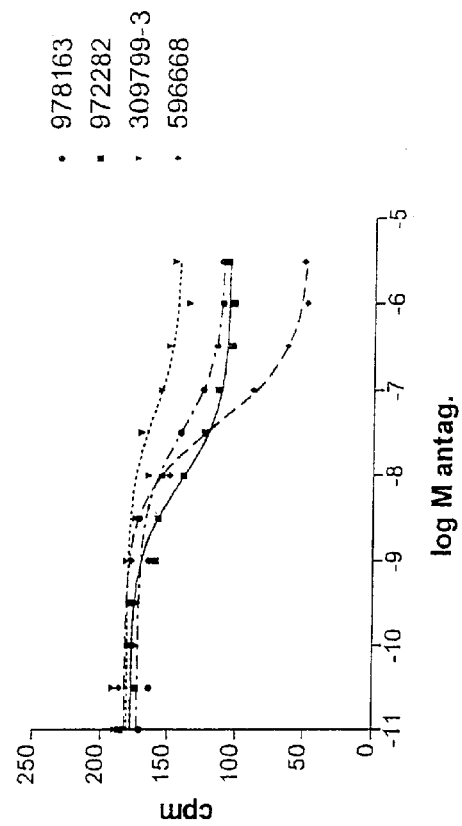
Figure 5D:
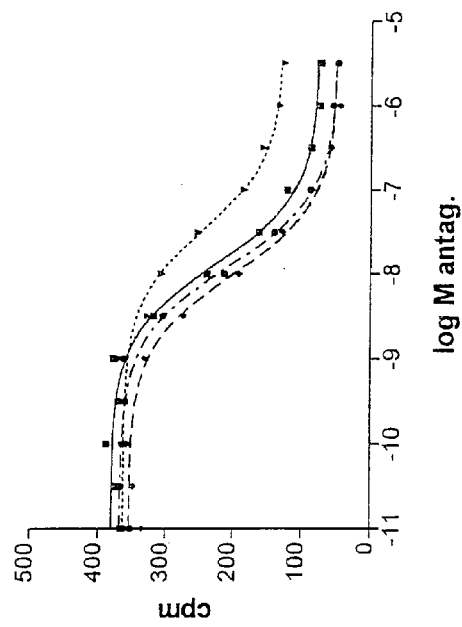
Figure 5E:
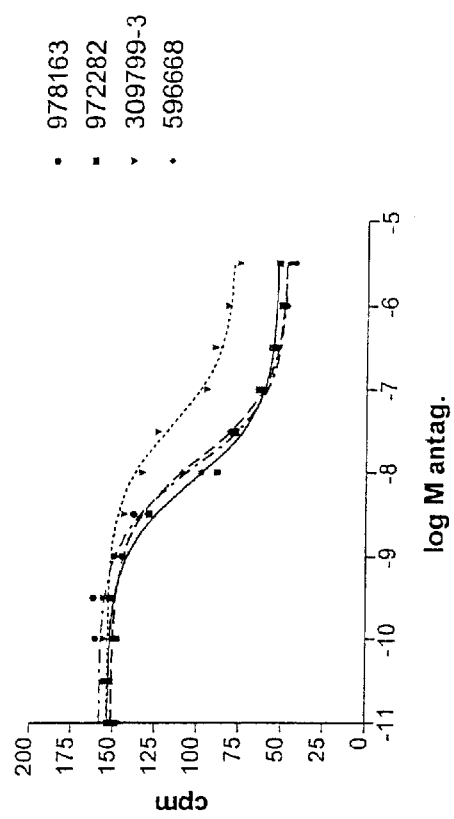
Figure 5E:
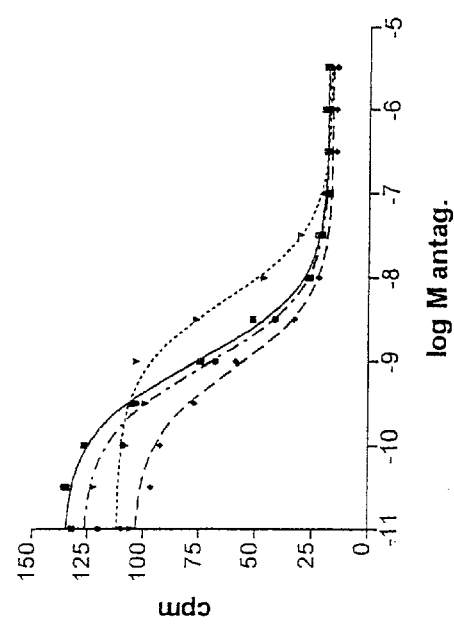
Figure 5F:
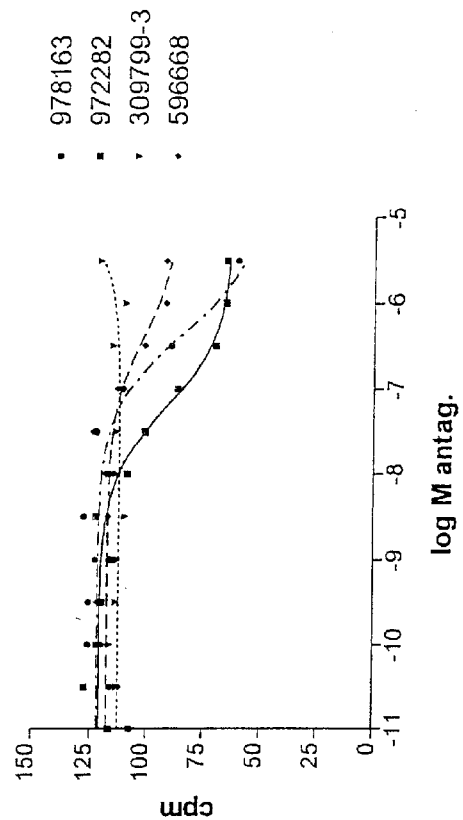
Figure 5F:
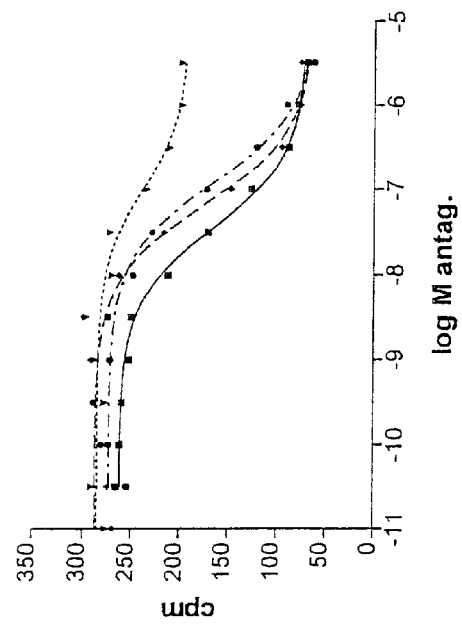

FIGS. 5A–B show the competition binding curves at each of the cloned receptors. In FIG. 5A, the binding of four peptides are shown, des-Arg$^{10}$-Kallidin [dAKd], Bradykinin [Bk], des-Arg$^{10}$-Leu$^9$-Kallidin [dALKd], and des-Arg$^9$-Bradykinin [dABk]. All of these receptors have strong affinity for dAKD but not BK and are, therefore, subtype 1 receptors. The potencies of the four peptides do vary at the different orthologues, however. FIG. 5B shows competition with four small molecules that have been identified. These also show various levels of activity at the different receptors.

What is claimed is:

1. A purified nucleic acid comprising a nucleotide sequence that encodes a bradykinin $B_1$ receptor having an amino acid sequence chosen from SEQ ID NO: 1, SEQ ID NO: 2, SEQ ID NO: 3, SEQ ID NO: 4, SEQ ID NO: 5, SEQ ID NO: 6.

2. A purified nucleic acid comprising a nucleotide sequence chosen from SEQ ID NO: 7, SEQ ID NO: 8, SEQ ID NO: 9, SEQ ID NO: 10, SEQ ID NO: 11, SEQID NO: 12.

3. An expression vector which comprises a nucleotide sequence that encodes a bradykinin $B_1$ receptor having an amino acid sequence chosen from SEQ ID NO: 1, SEQ ID NO: 2, SEQ ID NO: 3, SEQ ID NO: 4, SEQ ID NO: 5, SEQ ID NO: 6.

4. An expression vector which comprises a nucleotide sequence chosen from SEQ ID NO: 7, SEQ ID NO: 8, SEQ ID NO: 9, SEQ ID NO: 10, SEQ ID NO: 11, SEQ ID NO: 12.

5. A recombinant cell comprising the expression vector of claim 3.

6. A recombinant cell comprising the expression vector of claim 4.

7. A method for producing a recombinant host cell capable of expressing a bradykinin $B_1$ receptor, comprising:

(a) transfecting a suitable host cell with an expression vector which comprises a nucleotide sequence chosen from SEQ ID NO: 7, SEQ ID NO: 8, SEQ ID NO: 9, SEQ ID NO: 10, SEQ ID NO: 11, and SEQ ID NO: 12, and (b) maintaining said host cells under conditions in which said nucleotide sequence is expressed.

8. A method for producing a recombinant host cell capable of expressing a bradykinin $B_1$ receptor, comprising:

(a) transfecting suitable host cells with an expression vector which comprises a nucleotide sequence that encodes a bradykinin $B_1$ receptor having an amino acid sequence chosen from SEQ ID NO: 1, SEQ ID NO: 2, SEQ ID NO: 3, SEQ ID NO: 4, SEQ ID NO: 5, SEQ ID NO: 6; and (b) maintaining said host cells under conditions in which said nucleotide sequence is expressed.

* * * * *

SEQUENCE LISTING

<160> NUMBER OF SEQ ID NOS: 26

<210> SEQ ID NO 1
<211> LENGTH: 352
<212> TYPE: PRT
<213> ORGANISM: Cercopithecus pygerythrus

<400> SEQUENCE: 1

Met Ala Ser Trp Pro Pro Leu Glu Leu Gln Ser Ser Asn Gln Ser Gln
 1               5                   10                  15

```
Leu Phe Pro Gln Asn Ala Thr Ala Cys Asp Asn Ala Pro Glu Ala Trp
                20                  25                  30

Asp Leu Leu His Arg Val Leu Pro Thr Phe Ile Ile Ser Ile Cys Ser
            35                  40                  45

Phe Gly Leu Leu Gly Asn Leu Phe Val Leu Leu Val Phe Leu Leu Pro
        50                  55                  60

Arg Arg Arg Leu Asn Val Ala Glu Ile Tyr Leu Ala Asn Leu Ala Ala
 65                  70                  75                  80

Ser Asp Leu Val Phe Val Leu Gly Leu Pro Phe Trp Ala Glu Asn Ile
                85                  90                  95

Trp Asn Gln Phe Asn Trp Pro Phe Gly Ala Leu Leu Cys Arg Gly Ile
                100                 105                 110

Asn Gly Val Ile Lys Ala Asn Leu Phe Ile Ser Ile Phe Leu Val Val
            115                 120                 125

Ala Ile Ser Gln Asp Arg Tyr Cys Leu Leu Val His Pro Met Ala Ser
        130                 135                 140

Arg Arg Arg Gln Arg Arg Arg Gln Ala Arg Val Thr Cys Val Leu Ile
145                 150                 155                 160

Trp Val Val Gly Gly Leu Leu Ser Ile Pro Thr Phe Leu Leu Arg Ser
                165                 170                 175

Ile Gln Ala Val Pro Asp Leu Asn Ile Thr Ala Cys Ile Leu Leu Leu
                180                 185                 190

Pro His Glu Ala Trp His Phe Ala Arg Ile Val Glu Leu Asn Ile Leu
            195                 200                 205

Ala Phe Leu Leu Pro Leu Ala Ala Ile Val Phe Phe Asn Tyr His Ile
        210                 215                 220

Leu Ala Ser Leu Arg Gly Arg Glu Glu Val Ser Arg Thr Arg Cys Gly
225                 230                 235                 240

Gly Arg Lys Asp Ser Lys Thr Thr Ala Leu Ile Leu Thr Leu Val Val
                245                 250                 255

Ala Phe Leu Val Cys Trp Ala Pro Tyr His Phe Phe Ala Phe Leu Glu
                260                 265                 270

Phe Leu Phe Gln Val Gln Ala Ile Arg Ser Cys Phe Trp Glu Asp Phe
            275                 280                 285

Ile Asp Leu Gly Leu Gln Leu Ala Asn Phe Leu Ala Phe Thr Asn Ser
        290                 295                 300

Ser Leu Asn Pro Val Ile Tyr Val Phe Val Gly Arg Leu Phe Arg Thr
305                 310                 315                 320

Lys Val Trp Glu Leu Tyr Lys Gln Cys Thr Pro Lys Ser Leu Ala Pro
                325                 330                 335

Ile Ser Ser His Arg Lys Glu Ile Phe Gln Leu Phe Trp Arg Asn
                340                 345                 350

<210> SEQ ID NO 2
<211> LENGTH: 352
<212> TYPE: PRT
<213> ORGANISM: Macaca mulatta

<400> SEQUENCE: 2

Met Ala Ser Trp Pro Pro Leu Glu Leu Gln Ser Ser Asn Gln Ser Gln
  1               5                  10                  15

Leu Phe Pro Gln Asn Ala Thr Ala Cys Asp Asn Ala Pro Glu Ala Trp
                20                  25                  30

Asp Leu Leu His Arg Val Leu Pro Thr Phe Ile Ile Ser Ile Cys Ser
            35                  40                  45
```

```
Phe Gly Leu Leu Gly Asn Leu Phe Val Leu Val Phe Leu Leu Pro
         50                  55                  60

Arg Arg Arg Leu Asn Val Ala Glu Ile Tyr Leu Ala Asn Leu Ala Ala
 65                  70                  75                  80

Ser Asp Leu Val Phe Val Leu Gly Leu Pro Phe Trp Ala Glu Asn Ile
                 85                  90                  95

Trp Asn Gln Phe Asn Trp Pro Phe Gly Ala Leu Leu Cys Arg Val Ile
                100                 105                 110

Asn Gly Ile Ile Lys Ala Asn Leu Phe Ile Ser Ile Phe Leu Val Val
             115                 120                 125

Ala Ile Ser Gln Asp Arg Tyr Cys Val Leu Val His Pro Met Ala Ser
     130                 135                 140

Arg Arg Arg Gln Arg Arg Gln Ala Arg Val Thr Cys Val Leu Ile
145                 150                 155                 160

Trp Val Val Gly Gly Leu Leu Ser Ile Pro Thr Phe Leu Leu Arg Ser
                165                 170                 175

Ile Gln Ala Val Pro Asp Leu Asn Ile Thr Ala Cys Ile Leu Leu Leu
         180                 185                 190

Pro His Glu Ala Trp His Phe Ala Arg Ile Val Glu Leu Asn Ile Leu
     195                 200                 205

Ala Phe Leu Leu Pro Leu Ala Ile Ile Phe Phe Asn Tyr His Ile
 210                 215                 220

Leu Ala Ser Leu Arg Gly Arg Glu Val Ser Arg Thr Arg Cys Gly
225                 230                 235                 240

Gly Ser Lys Asp Ser Lys Thr Thr Ala Leu Ile Leu Thr Leu Val Val
                245                 250                 255

Ala Phe Leu Val Cys Trp Ala Pro Tyr His Phe Ala Phe Leu Glu
                260                 265                 270

Phe Leu Phe Gln Val Gln Ala Val Arg Gly Cys Phe Trp Glu Asp Phe
         275                 280                 285

Ile Asp Leu Gly Leu Gln Leu Ala Asn Phe Leu Ala Phe Thr Asn Ser
 290                 295                 300

Ser Leu Asn Pro Val Ile Tyr Val Phe Val Gly Arg Leu Phe Arg Thr
305                 310                 315                 320

Lys Val Trp Glu Leu Tyr Lys Gln Cys Thr Pro Lys Ser Leu Ala Pro
                325                 330                 335

Ile Ser Ser His Arg Lys Glu Ile Phe Gln Leu Phe Trp Arg Asn
             340                 345                 350

<210> SEQ ID NO 3
<211> LENGTH: 352
<212> TYPE: PRT
<213> ORGANISM: Tupaia minor

<400> SEQUENCE: 3

Met Ala Ala Gln Thr Leu Leu Glu Leu Gln Pro Ser Asn Gln Ser Gln
 1               5                  10                  15

Leu Ser Ala Leu Asn Thr Thr Ser Cys Asp Asn Ala Arg Glu Ala Trp
                 20                  25                  30

Asp Leu Leu Tyr Gln Val Leu Pro Ile Phe Ile Leu Thr Ile Cys Ala
             35                  40                  45

Phe Gly Leu Leu Gly Asn Leu Phe Val Leu Ser Val Phe Leu Leu Leu
         50                  55                  60

Arg Arg Arg Leu Thr Val Ala Glu Ile Tyr Leu Val Asn Leu Ala Ala
 65                  70                  75                  80
```

-continued

```
Ser Asp Leu Val Phe Val Leu Gly Leu Pro Phe Trp Ala Gln Asn Ile
             85                  90                  95

Trp Asn Gln Phe Asn Trp Pro Phe Gly Asp Leu Leu Cys Arg Val Val
            100                 105                 110

Asn Gly Val Ile Lys Ala Asn Leu Phe Ile Ser Ile Phe Leu Met Val
            115                 120                 125

Ala Ile Ser Gln Asp Arg Tyr Cys Val Leu Val His Pro Met Ala Ser
        130                 135                 140

Arg Arg Arg Arg Arg Arg Arg Ala Arg Ala Thr Cys Met Val Ile
145                 150                 155                 160

Trp Ala Val Gly Ala Leu Leu Ser Thr Pro Thr Phe Leu Leu Arg Ser
                165                 170                 175

Val Ser Ala Val Gln Asp Leu Asn Ile Ser Ala Cys Ile Leu Leu Leu
            180                 185                 190

Pro His Gln Ala Trp His Val Ala Arg Ile Val Glu Leu Asn Val Leu
        195                 200                 205

Gly Phe Leu Leu Pro Leu Ala Ala Ile Ile Phe Phe Asn Gly His Ile
    210                 215                 220

Leu Ala Ser Leu Arg Gly Gln Gly Glu Val Ser Gln Thr Arg Ile Gly
225                 230                 235                 240

Gly Pro Lys Asp Cys Lys Thr Thr Val Leu Ile Leu Thr Leu Val Ala
                245                 250                 255

Ala Phe Leu Val Cys Trp Ala Pro Tyr His Cys Phe Ala Phe Leu Glu
            260                 265                 270

Phe Leu Phe Gln Val Arg Ala Val Arg Gly Cys Phe Trp Glu Asp Phe
        275                 280                 285

Ile Asp Leu Gly Leu Gln Leu Ala Asn Phe Phe Ala Phe Thr Asn Ser
    290                 295                 300

Cys Leu Asn Pro Val Ile Tyr Val Phe Val Gly Arg Leu Phe Arg Thr
305                 310                 315                 320

Lys Val Trp Glu Leu Tyr Gln Gln Cys Thr Pro Arg Pro Ala Pro
                325                 330                 335

Leu Ser Ser Arg Arg Lys Glu Ile Leu Arg Arg Phe Trp Arg Asn
                340                 345                 350
```

<210> SEQ ID NO 4
<211> LENGTH: 320
<212> TYPE: PRT
<213> ORGANISM: Canis familiaris

<400> SEQUENCE: 4

```
Met Ala Ser Arg Ala Pro Leu Glu Leu Leu Pro Leu Asn Arg Ser Gln
  1               5                  10                  15

Leu Ser Pro Pro Asn Ala Thr Thr Cys Asp Asp Ala Pro Glu Ala Trp
             20                  25                  30

Asp Leu Leu His Arg Val Leu Pro Ser Val Ile Ile Ile Ile Cys Val
         35                  40                  45

Cys Gly Leu Leu Gly Asn Leu Val Leu Ala Val Leu Leu Arg Pro
     50                  55                  60

Arg Arg Arg Leu Asn Val Ala Glu Met Tyr Leu Ala Asn Leu Ala Ala
65                  70                  75                  80

Ser Asp Leu Val Phe Val Leu Gly Leu Pro Phe Trp Ala Ala Asn Ile
             85                  90                  95

Ser Asn Gln Phe Arg Trp Pro Phe Gly Gly Leu Leu Cys Arg Leu Val
            100                 105                 110
```

```
Asn Gly Val Ile Lys Ala Asn Leu Phe Ile Ser Ile Phe Leu Val Val
        115                 120                 125

Ala Ile Ser Arg Asp Arg Tyr Arg Ala Leu Val His Pro Met Ala Thr
    130                 135                 140

Arg Arg Arg Arg Gln Ala Arg Ala Thr Cys Val Leu Ile Trp Val Ala
145                 150                 155                 160

Gly Ser Leu Leu Ser Val Pro Thr Phe Leu Phe Arg Ser Ile Glu Ala
                165                 170                 175

Val Pro Glu Leu Asn Asn Asp Ser Ala Cys Val Leu Leu His Pro Pro
            180                 185                 190

Gly Ala Trp His Val Ala Arg Met Val Glu Leu Asn Val Leu Gly Phe
                195                 200                 205

Leu Leu Pro Leu Ala Ala Ile Val Phe Phe Asn Cys His Ile Leu Ala
    210                 215                 220

Ser Leu Arg Gly Arg Pro Glu Val Arg Gly Ala Arg Cys Gly Gly Pro
225                 230                 235                 240

Pro Asp Gly Arg Thr Thr Ala Leu Ile Leu Thr Phe Val Ala Ala Phe
                245                 250                 255

Leu Val Cys Trp Thr Pro Tyr His Phe Phe Ala Phe Leu Glu Phe Leu
                260                 265                 270

Thr Gln Val Gln Val Val Arg Gly Cys Phe Trp Glu Asn Phe Lys Asp
            275                 280                 285

Leu Gly Leu Gln Tyr Ala Ser Phe Phe Ala Phe Ile Asn Ser Cys Leu
    290                 295                 300

Asn Pro Val Ile Tyr Val Phe Val Gly Arg Leu Phe Arg Thr Lys Val
305                 310                 315                 320

<210> SEQ ID NO 5
<211> LENGTH: 350
<212> TYPE: PRT
<213> ORGANISM: Artificial Sequence
<220> FEATURE:
<223> OTHER INFORMATION: Description of Artificial Sequence:  chimeric
      molecule consisting of amino acids 1-315 of dog bradykinin B1
      receptor (BKR) and amino acids 319-353 of human BKR

<400> SEQUENCE: 5

Met Ala Ser Arg Ala Pro Leu Glu Leu Leu Pro Leu Asn Arg Ser Gln
1               5                   10                  15

Leu Ser Pro Pro Asn Ala Thr Thr Cys Asp Asp Ala Pro Glu Ala Trp
                20                  25                  30

Asp Leu Leu His Arg Val Leu Pro Ser Val Ile Ile Ile Ile Cys Val
            35                  40                  45

Cys Gly Leu Leu Gly Asn Leu Val Leu Ala Val Leu Leu Arg Pro
    50                  55                  60

Arg Arg Arg Leu Asn Val Ala Glu Met Tyr Leu Ala Asn Leu Ala Ala
65                  70                  75                  80

Ser Asp Leu Val Phe Val Leu Gly Leu Pro Phe Trp Ala Ala Asn Ile
                85                  90                  95

Ser Asn Gln Phe Arg Trp Pro Phe Gly Gly Leu Leu Cys Arg Leu Val
                100                 105                 110

Asn Gly Val Ile Lys Ala Asn Leu Phe Ile Ser Ile Phe Leu Val Val
        115                 120                 125

Ala Ile Ser Arg Asp Arg Tyr Arg Ala Leu Val His Pro Met Ala Thr
    130                 135                 140
```

```
Arg Arg Arg Arg Gln Ala Arg Ala Thr Cys Val Leu Ile Trp Val Ala
145                 150                 155                 160

Gly Ser Leu Leu Ser Val Pro Thr Phe Leu Phe Arg Ser Ile Glu Ala
                165                 170                 175

Val Pro Glu Leu Asn Asn Asp Ser Ala Cys Val Leu Leu His Pro Pro
            180                 185                 190

Gly Ala Trp His Val Ala Arg Met Val Glu Leu Asn Val Leu Gly Phe
        195                 200                 205

Leu Leu Pro Leu Ala Ala Ile Val Phe Phe Asn Cys His Ile Leu Ala
    210                 215                 220

Ser Leu Arg Gly Arg Pro Glu Val Arg Gly Ala Arg Cys Gly Gly Pro
225                 230                 235                 240

Pro Asp Gly Arg Thr Thr Ala Leu Ile Leu Thr Phe Val Ala Ala Phe
                245                 250                 255

Leu Val Cys Trp Thr Pro Tyr His Phe Phe Ala Phe Leu Glu Phe Leu
            260                 265                 270

Thr Gln Val Gln Val Val Arg Gly Cys Phe Trp Glu Asn Phe Lys Asp
        275                 280                 285

Leu Gly Leu Gln Tyr Ala Ser Phe Phe Ala Phe Ile Asn Ser Cys Leu
    290                 295                 300

Asn Pro Val Ile Tyr Val Phe Val Gly Arg Leu Phe Arg Thr Lys Val
305                 310                 315                 320

Trp Glu Leu Tyr Lys Gln Cys Thr Pro Lys Ser Leu Ala Pro Ile Ser
                325                 330                 335

Ser Ser His Arg Lys Glu Ile Phe Gln Leu Phe Trp Arg Asn
                340                 345                 350

<210> SEQ ID NO 6
<211> LENGTH: 353
<212> TYPE: PRT
<213> ORGANISM: Sus sp.

<400> SEQUENCE: 6

Met Ala Ser Gln Thr Leu Val Val Phe Gln Ala Ser Asn Gln Ser Gln
1               5                   10                  15

Leu Pro Pro Pro Asn Ala Thr Leu Cys Asp Gly Ala Gln Glu Ala Trp
                20                  25                  30

His Leu Leu His Lys Val Leu Pro Thr Cys Val Val Ala Ile Cys Ser
            35                  40                  45

Gly Gly Leu Leu Gly Asn Leu Phe Val Leu Ser Val Phe Leu Val Pro
        50                  55                  60

Arg Arg Arg Leu Asn Ala Ala Glu Ile Tyr Leu Ala His Leu Ala Ala
65                  70                  75                  80

Ser Asp Leu Val Phe Ala Leu Gly Leu Pro Phe Trp Ala Glu Thr Ile
                85                  90                  95

Arg Asn Gly Phe His Trp Pro Phe Gly Ala Pro Leu Cys Arg Val Val
            100                 105                 110

Asn Gly Val Ile Lys Ala Asn Leu Phe Ile Ser Ile Phe Leu Val Val
        115                 120                 125

Ala Ile Ser Arg Asp Arg Tyr Arg Ala Leu Val His Pro Val Ala Ser
    130                 135                 140

Trp Arg Arg Arg Arg Arg His Trp Ala Gln Ala Thr Cys Val Leu
145                 150                 155                 160

Ile Trp Thr Ala Gly Gly Leu Leu Ser Ile Pro Thr Phe Leu Leu Arg
                165                 170                 175
```

Ser Val Gln Val Val Pro Glu Leu Asn Val Ser Ala Cys Val Leu Pro
            180                 185                 190

Phe Pro His Glu Ala Trp Ala Phe Val Arg Thr Val Glu Leu Asn Val
            195                 200                 205

Leu Gly Phe Leu Leu Pro Leu Ala Ala Ile Leu Phe Phe Asn Tyr His
            210                 215                 220

Ile Leu Ala Ala Leu Arg Gly Arg Glu Gln Leu Ser Arg Thr Arg Cys
225                 230                 235                 240

Gly Gly Pro Arg Asp Gly Lys Thr Thr Ala Leu Ile Leu Thr Leu Val
                245                 250                 255

Ala Val Phe Leu Leu Cys Trp Thr Pro Tyr His Val Cys Ala Phe Leu
            260                 265                 270

Glu Phe Leu Leu His Val Arg Ala Ile Arg Gly Cys Phe Trp Glu Asp
            275                 280                 285

Phe Thr Asp Leu Gly Leu Gln Tyr Thr Asn Phe Phe Ala Phe Ile Asn
            290                 295                 300

Ser Cys Leu Asn Pro Val Ile Tyr Val Phe Trp Gly Gln Leu Phe Arg
305                 310                 315                 320

Thr Lys Ile Trp Glu Leu Tyr His Arg Cys Leu Pro Arg Lys Leu Thr
                325                 330                 335

Ala Val Ser Ser Arg Arg Lys Glu Ile Phe Gln Ile Phe Trp Arg
            340                 345                 350
Asn

<210> SEQ ID NO 7
<211> LENGTH: 1059
<212> TYPE: DNA
<213> ORGANISM: Cercopithecus pygerythrus

<400> SEQUENCE: 7

```
atggcatcct ggccccctct agagctccag tcctccaacc agagccagct gttccctcaa      60
aatgctacag cctgtgacaa tgctccggaa gcctgggacc tgctgcacag agtgctgccg     120
acatttatca tctccatctg ttccttcggc ctcctaggga acctttttcgt cctattggtc    180
ttcctcctgc ccaggcggcg actgaacgtg gcagaaatct acctggccaa cctggcggcc    240
tctgatctgt gtttgtcttg ggcttgcct ttctgggcag agaatatttg gaaccagttt     300
aactggcctt tcggagccct cctctgccgt ggcatcaacg tgtcatcaa ggccaatttg      360
ttcatcagca tcttcctggt ggtggccatc agccaggacc gctactgcct gctggtgcac    420
cctatggcca gccggaggcg gcagcgacgg aggcaggccc gggtcacctg tgtgctcatc    480
tgggttgtgg gtggcctctt gagcatcccc acattcctgc tgcgatccat ccaagccgtc    540
ccagatctga acatcaccgc ctgcatcctg ctcctccccc atgaggcctg gcactttgca    600
aggattgtgg agttaaatat tctggctttc tcctaccac tggctgcgat cgtcttcttc     660
aactaccaca tcttggcctc cctgcgaggg cgggaggagg tcagcaggac aaggtgcggg    720
ggccgcaagg atagcaagac acagcgctg atcctcacgc tcgtggtggc cttcctggtc     780
tgctgggccc cttaccactt ctttgccttc ctggaattct tattccaggt gcaagcaatc    840
cgaagctgct tgggagga cttcattgac ctgggcctgc aattggccaa cttcttggcc      900
ttcaccaaca gctccctgaa tccagtcatt tatgtctttg tgggccggct cttcaggacc    960
aaggtctggg aactttataa acaatgcacc cctaaaagtc ttgctccaat atcttcatcc   1020
cacaggaaag aaatcttcca actttttctgg cggaattaa                          1059
```

<210> SEQ ID NO 8
<211> LENGTH: 1059
<212> TYPE: DNA
<213> ORGANISM: Macaca mulatta

<400> SEQUENCE: 8

| | | | | | |
|---|---|---|---|---|---|
| atggcatcct | ggcccctct | agagctccag | tcctccaacc | agagccagct | gttccctcaa | 60 |
| aatgctacag | cctgtgacaa | tgctccagaa | gcctgggacc | tgctgcacag | agtgctgccg | 120 |
| acatttatca | tctccatctg | ttccttcggc | ctcctaggga | accttttcgt | cctgttggtc | 180 |
| ttcctcctgc | ccaggcggcg | actgaacgtg | gcagaaatct | acctggccaa | cctggcggcc | 240 |
| tctgatctgg | tgtttgtctt | gggtttgcct | ttctgggcag | agaacatttg | gaaccagttt | 300 |
| aactggcctt | tcggagccct | cctctgccgt | gtcatcaacg | gcatcatcaa | ggctaatttg | 360 |
| ttcatcagca | tcttcctggt | ggtggccatc | agccaggacc | gctactgcgt | gctggtgcac | 420 |
| cctatggcca | gccggaggcg | gcagcggcgg | aggcaggccc | gggtcacctg | cgtgctcatc | 480 |
| tgggttgtgg | ggggcctctt | gagcatcccc | acattcctgc | tgcgatccat | ccaagccgtc | 540 |
| ccagatctga | acatcaccgc | ctgcatcctg | ctcctcccgc | atgaggcctg | gcactttgcg | 600 |
| aggattgtgg | agttaaatat | tctggctttc | ctcctaccac | tggctgcgat | catcttcttc | 660 |
| aactaccaca | tcttggcctc | cctgcgaggg | cgggaggagg | tcagcaggac | aaggtgcggg | 720 |
| ggcagcaagg | atagcaagac | cacagcgctg | atcctcacgc | tcgtggtggc | cttcctggtc | 780 |
| tgctgggccc | cttaccactt | ctttgccttc | ctggaattct | tattccaggt | gcaagcagtc | 840 |
| cgaggctgct | tttgggagga | cttcattgac | ctgggcctgc | aactggccaa | cttcttggcc | 900 |
| ttcaccaaca | gctccctgaa | tccagtcatt | tatgtctttg | tgggccggct | cttcaggacc | 960 |
| aaggtctggg | aactttataa | acaatgcacc | cctaaaagtc | ttgctccaat | atcttcatcc | 1020 |
| cacaggaaag | aaatcttcca | actttctgg | cggaattaa | | | 1059 |

<210> SEQ ID NO 9
<211> LENGTH: 1059
<212> TYPE: DNA
<213> ORGANISM: Tupaia minor

<400> SEQUENCE: 9

| | | | | | |
|---|---|---|---|---|---|
| atggcagccc | agacactcct | ggaactccag | ccctccaacc | agagccagct | gtccgctctc | 60 |
| aacaccacgt | cctgtgacaa | tgctcgggaa | gcctgggacc | tgctatacca | agtgctacca | 120 |
| attttcatcc | tcaccatctg | cgccttcggc | ctcctgggaa | acctgttcgt | cctgtctgtc | 180 |
| ttcctcctgc | tcaggcgccg | gctgactgtg | gcagaaatct | acctggtcaa | cctggcgget | 240 |
| tccgacctgg | tgtttgtcct | gggcttgccc | ttctgggcac | agaacatctg | gaaccaattc | 300 |
| aactggcctt | ttggggacct | cctctgccgc | gtcgtcaacg | gagtcatcaa | ggccaacttg | 360 |
| ttcatcagca | tctttctgat | ggtggccatc | agccaggacc | gctactgcgt | gctggtgcat | 420 |
| cccatggcca | gccgcaggcg | gcggcggcg | cggcgggccc | gggccacctg | catggtcatc | 480 |
| tgggccgtgg | gggccctcct | gagcaccccg | acgttcctgc | tgcgatccgt | cagtgccgtc | 540 |
| caggatctga | acatctctgc | ctgcatcttg | ctgcttccac | accaggcctg | gcacgtagcg | 600 |
| aggatcgtgg | agctgaatgt | gctggggttc | ctcctgccct | tggctgcaat | catcttcttc | 660 |
| aacggccaca | tcctggcctc | actgcgaggg | caggggggagg | tcagccagac | acggattggg | 720 |
| ggccccaagg | actgcaagac | caccgtgctg | atcctcacgc | tcgtggctgc | tttcctggtc | 780 |
| tgctgggccc | cctaccactg | cttcgccttc | ctggagttcc | tgttccaggt | gcgagctgtg | 840 |

| | |
|---|---|
| cgaggctgct tctgggaaga cttcatcgac ctgggcctgc agctggccaa cttctttgct | 900 |
| ttcaccaaca gctgcctgaa cccggtgatc tatgtcttcg tgggccggct cttcaggacc | 960 |
| aaggtctggg aactgtacca acaatgcacc ccgagacgac cagctcccct gtcctcgtcc | 1020 |
| cgcaggaaag aaatcctccg gcgtttctgg cggaattaa | 1059 |

<210> SEQ ID NO 10
<211> LENGTH: 960
<212> TYPE: DNA
<213> ORGANISM: Canis familiaris

<400> SEQUENCE: 10

| | |
|---|---|
| atggcatcgc gggccccccct ggagctcctg cccctgaacc ggagccagct gtcgcctcca | 60 |
| aacgccacga cctgtgacga tgctccagaa gcctgggacc tgctgcacag agtcttacca | 120 |
| tcagtcatca tcatcatctg tgtctgcggg ctgctgggaa accttctggt gctggcggtc | 180 |
| ttgctccggc cccggcggcg tctgaacgtg gccgaaatgt acctggccaa cctggccgcc | 240 |
| tccgacctgg tgtttgtcct gggcttgccc ttctgggcgg cgaacatctc gaaccagttc | 300 |
| cgctggccct tcgggggcct cctctgccgc ctcgtcaacg gagtcatcaa ggccaatttg | 360 |
| ttcatcagca tcttcctggt ggtggccatc agccgggacc gctaccgcgc gctggtgcac | 420 |
| cccatggcca cccggcggcg gcgacaggcc cgggccacct gcgtgctcat ctgggtggcg | 480 |
| ggcagcctcc tgagcgtccc caccttcctg ttccgctcca tcgaagctgt gcccgagctg | 540 |
| aacaacgaca gcgcctgcgt cctgctgcac ccgcccgggg cctggcacgt cgcgaggatg | 600 |
| gtggagctga acgtgctggg gttcctgctg ccgctggctg ccatcgtctt cttcaactgc | 660 |
| cacatcctgg cctccctgcg cgggcggccc gaggtgcgcg gggcgcggtg cggggggccc | 720 |
| cccgacggca ggaccacggc gctcatcctc accttcgtgg ccgccttcct ggtgtgctgg | 780 |
| accccctacc acttcttcgc cttcctggaa ttcctgacgc aggtgcaggt cgtccgcggc | 840 |
| tgcttctggg agaatttcaa agacctgggc ctgcagtacg ccagcttctt tgccttcatc | 900 |
| aacagctgcc tgaaccccgt catctacgtc ttcgtgggcc ggctcyttaa gaccarggty | 960 |

<210> SEQ ID NO 11
<211> LENGTH: 1053
<212> TYPE: DNA
<213> ORGANISM: Artificial Sequence
<220> FEATURE:
<223> OTHER INFORMATION: Description of Artificial Sequence: chimeric
    DNA encoding amino acids 1-315 of dog BKR and amino acids 319-353
    of human BKR

<400> SEQUENCE: 11

| | |
|---|---|
| atggcatcgc gggccccccct ggagctcctg cccctgaacc ggagccagct gtcgcctcca | 60 |
| aacgccacga cctgtgacga tgctccagaa gcctgggacc tgctgcacag agtcttacca | 120 |
| tcagtcatca tcatcatctg tgtctgcggg ctgctgggaa accttctggt gctggcggtc | 180 |
| ttgctccggc cccggcggcg tctgaacgtg gccgaaatgt acctggccaa cctggccgcc | 240 |
| tccgacctgg tgtttgtcct gggcttgccc ttctgggcgg cgaacatctc gaaccagttc | 300 |
| cgctggccct tcgggggcct cctctgccgc ctcgtcaacg gagtcatcaa ggccaatttg | 360 |
| ttcatcagca tcttcctggt ggtggccatc agccgggacc gctaccgcgc gctggtgcac | 420 |
| cccatggcca cccggcggcg gcgacaggcc cgggccacct gcgtgctcat ctgggtggcg | 480 |
| ggcagcctcc tgagcgtccc caccttcctg ttccgctcca tcgaagctgt gcccgagctg | 540 |
| aacaacgaca gcgcctgcgt cctgctgcac ccgcccgggg cctggcacgt cgcgaggatg | 600 |

| | |
|---|---|
| gtggagctga acgtgctggg gttcctgctg ccgctggctg ccatcgtctt cttcaactgc | 660 |
| cacatcctgg cctccctgcg cgggcggccc gaggtgcgcg gggcgcggtg cgggggggccc | 720 |
| cccgacggca ggaccacggc gctcatcctc accttcgtgg ccgccttcct ggtgtgctgg | 780 |
| accccctacc acttcttcgc cttcctggaa ttcctgacgc aggtgcaggt cgtccgcggc | 840 |
| tgcttctggg agaatttcaa agacctgggc ctgcagtacg ccagcttctt tgccttcatc | 900 |
| aacagctgcc tgaaccccgt catctacgtc ttcgtgggcc ggctcttcag gaccaaggtc | 960 |
| tgggaacttt ataaacaatg caccccctaaa agtcttgctc aatatcttc atcccatagg | 1020 |
| aaagaaatct tccaactttt ctggcggaat taa | 1053 |

<210> SEQ ID NO 12
<211> LENGTH: 1062
<212> TYPE: DNA
<213> ORGANISM: Sus sp.

<400> SEQUENCE: 12

| | |
|---|---|
| atggcctccc agaccctcgt ggtgttccag gcctccaacc agagccagct cccacctcca | 60 |
| aatgccacgc tgtgtgacgg tgctcaggaa gcctggcacc tgctgcacaa ggtgctaccg | 120 |
| acttgcgtcg tggccatctg ctcgggcggc ctgctgggaa acctcttcgt gctgtcggtc | 180 |
| ttcctcgtgc ctcgacggcg tctgaacgcg gcggaaatct acctggccca cctggccgct | 240 |
| tctgacctgg tgttcgcctt gggcttgccc ttctgggccg agaccatccg gaacggattc | 300 |
| cactggcctt tcgagccccc cctctgccgc gtggtcaacg cgtcatcaa ggccaacctg | 360 |
| ttcatcagca tcttcctggt ggtggccatc agccgggacc gctaccgcgc gctggtgcac | 420 |
| cccgtggcca gctggaggcg gcggcggcgg cgccactggg cccaggccac ctgcgtgctc | 480 |
| atctggacgg cgggggggcct cctgagcatc cccacgttcc tgctgcgctc cgtccaagtg | 540 |
| gtcccggagc tgaacgtctc cgcctgcgtg ctgcccttcc ccacgaggc ctgggccttc | 600 |
| gtcaggacgg tggagttgaa cgtgctgggc tttctcctcc cgctggctgc catcctcttc | 660 |
| ttcaactatc acatcctggc agccctgcgg gggcgggagc agctcagcag acaaggtgc | 720 |
| gggggcccca gggatggcaa gaccacggcg ctgatcctca cgctcgtggc cgtcttcctg | 780 |
| ctctgctgga ccccgtacca cgtctgtgcc ttcctggaat tcctgctcca cgtgcgggcc | 840 |
| atccgaggct gcttctggga ggatttcacc gacctgggct tgcagtacac caacttcttt | 900 |
| gctttcatca acagctgcct aaatccagtc atctacgtct tttggggcca gcttttcaga | 960 |
| accaagatct gggaactgta tcaccgatgc ctccccagaa agctcactgc cgtgtcctcg | 1020 |
| tcccgtagga aagaaatctt ccaaattttc tggcggaatt aa | 1062 |

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:sense primer

<400> SEQUENCE: 13

| | |
|---|---|
| tgtycmkkyc rrgtcactgt gsatggc | 27 |

<210> SEQ ID NO 14
<211> LENGTH: 21
<212> TYPE: DNA
<213> ORGANISM: Artificial Sequence

```
<220> FEATURE:
<223> OTHER INFORMATION: Description of Artificial Sequence:antisense
      primer

<400> SEQUENCE: 14
gctgytttaa ttccgccaga a                                            21

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:sense primer

<400> SEQUENCE: 15
ggactagtac caccatggca tcatcctggc                                   30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:antisense
      primer

<400> SEQUENCE: 16
gcgtcgacgg ttcaatgctg ttttaattcc gcc                               33

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:sense primer

<400> SEQUENCE: 17
gcatgccacc atggcgtccg aggtcttgtt g                                 31

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:antisense
      primer

<400> SEQUENCE: 18
tgacttataa agtccccaga accctg                                       26

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence:sense primer

<400> SEQUENCE: 19
ataggtaccg ccaccatggc atcctggccc cctctagag                         39

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:antisense
      primer
```

```
<400> SEQUENCE: 20
gcgctcgagg ctgttttaat tccgccagaa                                   30

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:sense primer

<400> SEQUENCE: 21
ataggtaccg ccaccatggc agcccagaca ctcctg                            36

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:antisense
      primer

<400> SEQUENCE: 22
gcgctcgagt taattccgcc agaaamgcc                                    29

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence:sense primer

<400> SEQUENCE: 23
ataggtaccg ccaccatggc ctcccagacc ctcgtg                            36

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:antisense
      primer

<400> SEQUENCE: 24
gcgctcgagg ctgttttaat tccgccagaa                                   30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence:sense primer

<400> SEQUENCE: 25
ataggtaccg ccaccatggc atcgcgggcc ccctg                             36

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:antisense
      primer

<400> SEQUENCE: 26
raccytggtc ytrargagcc ggcc                                         24
```